(12) United States Patent
Ghetti et al.

(10) Patent No.: US 7,332,643 B2
(45) Date of Patent: Feb. 19, 2008

(54) FERRITIN LIGHT SUBUNIT VARIANT-ENCODING NUCLEIC ACIDS, POLYPEPTIDES, TRANSGENIC ANIMALS COMPRISING THE SAME, ANTIBODIES THERETO, AND METHODS OF USE THEREOF

(75) Inventors: Bernardino Ghetti, Indianapolis, IN (US); Ruben Vidal, Indianapolis, IN (US)

(73) Assignee: Indiana University & Technology Corp., Indianapolis, IN (US)

( * ) Notice: Subject to any disclaimer, the term of this patent is extended or adjusted under 35 U.S.C. 154(b) by 397 days.

(21) Appl. No.: 10/684,742

(22) Filed: Oct. 14, 2003

(65) Prior Publication Data

US 2004/0259107 A1 Dec. 23, 2004

Related U.S. Application Data

(60) Provisional application No. 60/418,126, filed on Oct. 11, 2002.

(51) Int. Cl.
*G01N 33/00* (2006.01)
*A01K 67/00* (2006.01)
*A01K 67/027* (2006.01)
*C07H 21/04* (2006.01)
*A01N 63/00* (2006.01)

(52) U.S. Cl. .............................. 800/3; 800/13; 800/18; 536/23.5; 536/24.1; 424/93.21

(58) Field of Classification Search .................. 800/13, 800/14, 18, 3; 536/23.5, 24.1, 23.1; 424/93.21
See application file for complete search history.

(56) References Cited

OTHER PUBLICATIONS

Kappel et al., 1992, Current Opinion in Biotechnology, vol. 3, p. 548-553.*
Wall, R. J., 1996, Theriogenology, vol. 45, p. 57-68.*
Strojek et al., 1988, Genetic Engineering: Principles and Methods, vol. 10, pp. 221-246.*
Sigmund, C., Jun. 2000, Arterioscler. Thromb. Vasc. Biol., p. 1425-1429.*
Mogil et al., 1999, Pain, vol. 80, pp. 67-82.*
Houdebine, L-M., 2002, Journal of Biotechnology, vol. 98, p. 145-160.*
Mercier et al., 1997, "The modification of milk protein composition through transgenesis: progress and problems," In: Transgenic Animals: Generation and use, Ed. Houdebine LM, Harwood Academic Publishers, The Netherlands pp. 473-482.*
Chinnery, P.F. et al. "Neuroferritinopathy in a French family with late onset dominant dystonia"; J. Med Genet., 40(5): e69 (2003).
Crompton, D.E. et al. "Neuoferritinopathy: a window on the role of iron in neurodegeneration"; Blood Cells Mol Dis., 29(3): 522-31 (2002).
Curtis, A.R. et al. "Mutation in the gene encoding ferritin light polypeptide causes dominant adult-onset basal ganglia disease"; Nat Genet., 28(4): 350-4 (2001).
Granier, T. et al. "Structure of mouse L-chain ferritin at 1.6 A resolution"; Acta Crystallogr D Biol Crystallogr., 57(Pt 11): 1491-7 (2001).
LaVaute, T. et al. "Targeted deletion of the gene encoding iron regulatory protein-2 causes misregulation of iron metabolism and neurodegenerative disease in mice"; Nat Genet., 27(2): 209-14 (2001).
Wills, A.J. et al. "Palatal tremor and cognitive decline in neuroferritinopathy"; J Neurol Neurosurg Psychiatry, 73(1): 91-2 (2002).
Jappelli, R. et al. "Cooperativity of mutational effects within a six amino acid residues substitution that induces a major conformational change in human H ferritin"; Biochem Biophys Res Commun., 250(2): 342-6 (1998).
Jappelli, R. et al. "Loop mutations can cause a substantial conformational change in the carboxy terminus of the ferritin protein"; J Mol Biol, 227(2): 532-43 (1992).
Delisle, M.B. et al. "A Neurodegenerative Disease With Intranuclear Deposits: Clinical and Neuropathologic Studies"; J Neuropathol Exp Neurol, 60: 514 (2001).
Vidal, R. et al. "A Neurodegenerative Disease With Intranuclear Protein Deposits: Electron Microscopic and Biochemical Studies"; J Neuropathol Exp Neurol, 60:515 (2001).

* cited by examiner

*Primary Examiner*—Shin-Lin Chen
(74) *Attorney, Agent, or Firm*—Dann, Dortman, Herrell & Skillman, P.C.; Kathleen D. Rigaut, J.D.

(57) ABSTRACT

Nucleic acids encoding a novel ferritin light chain variant, a ferritin light chain variant polypeptide, ferritin light chain variant polypeptide-specific antibodies, and methods of use thereof are provided herein. Also provided are methods to screen and identify agents capable of modulating the activity of the ferritin light chain variant.

4 Claims, 17 Drawing Sheets

Figure 2A-D
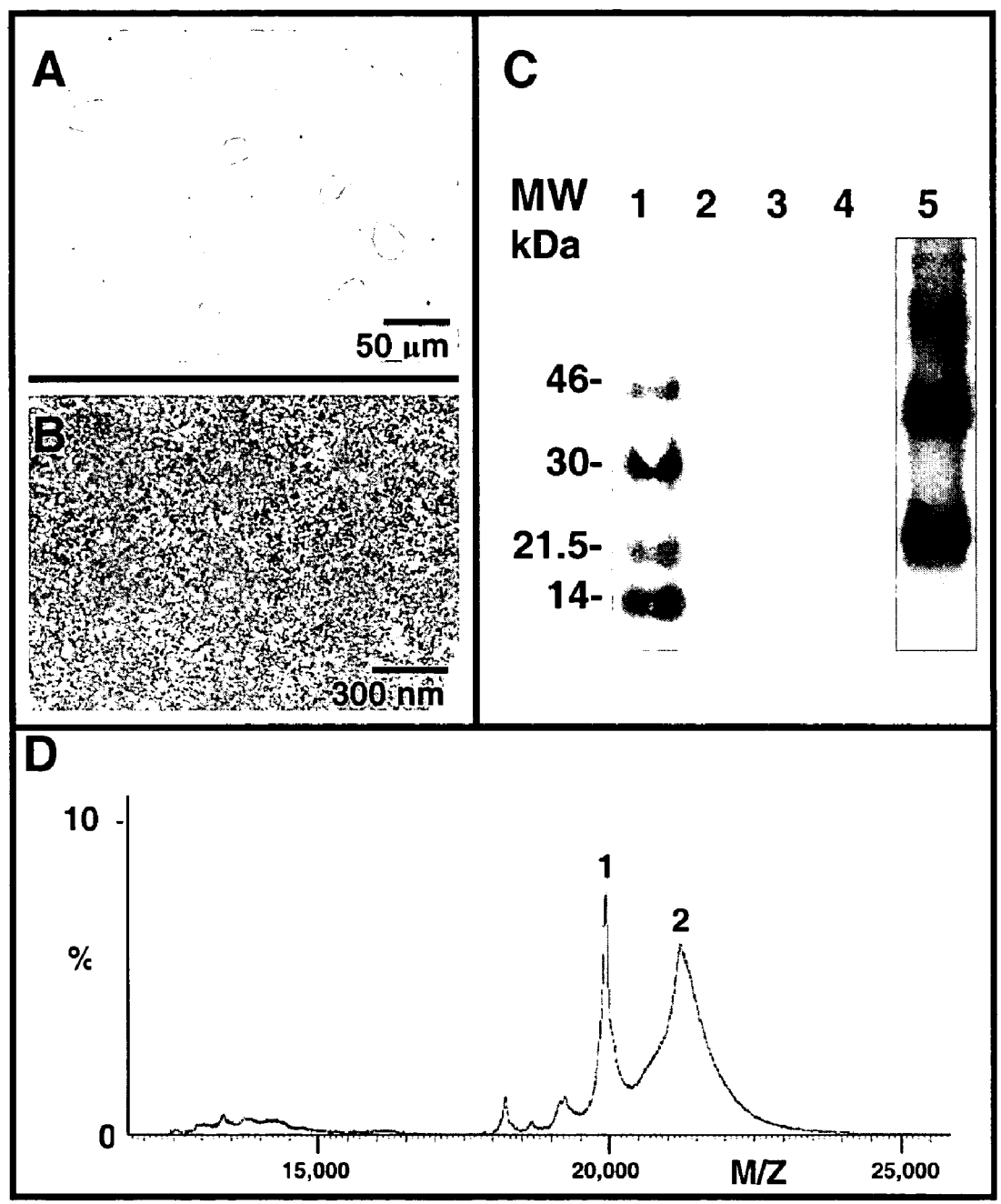

Figure 3A-E
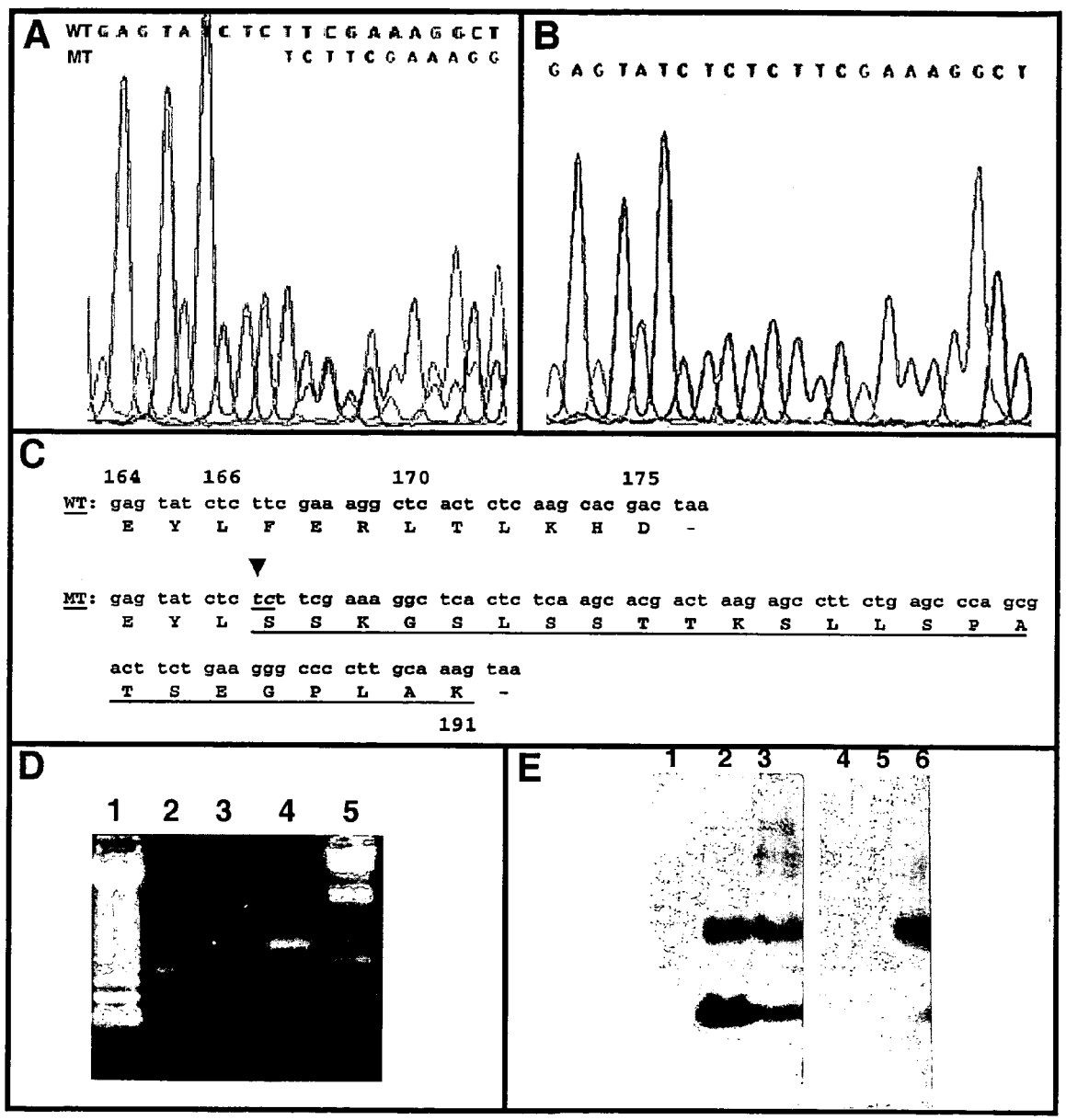

Figure 4

Nucleic acid sequence of FTL variant (SEQ ID NO:1)

atgagctcccagattcgtcagaattattccaccgacgtggaggcagcc gtcaacagcctggtcaatttgtacctgcaggcctcctacacctacctctctctgggcttc tatttcgaccgcgatgatgtggctctggaaggcgtgagccacttcttccgcgaattggcc gaggagaagcgcgagggctacgagcgtctcctgaagatgcaaaaccagcgtggcggccgc gctctcttccaggacatcaagaagccagctgaagatgagtggggtaaacccagacgcc atgaaagctgccatggccctggagaaaaagctgaaccaggcccttttggatcttcatgcc ctgggttctgcccgcacggaccccatctctgtgacttcctggagactcacttcctagat gaggaagtgaagcttatcaagaagatgggtgaccacctgaccaacctccacaggctgggt ggcccggaggctgggctgggcgagtatctctcttcgaaaggctcactctcaagcacgact aagagccttctgagcccagcgacttctgaagggccccttgcaaagtaa

Figure 5

Amino acid sequence of FLT variant (SEQ ID NO: 2)

A fragment of exon 4 encoding the FTL variant (SEQ ID NO: 3)

ctctgtgacttcctggagactcacttcctagatgaggaagtgaagcttatcaagaagatg

Figure 7A

Nucleic acid sequence of wildtype FLT (SEQ ID NO: 13)

ccaaccatgagctcccagattcgtcagaattattccaccgacgtggaggcagccgtcaac agcctggtcaatttgtacctgcaggcctcctacacctacctctctctgggcttctatttc gaccgcgatgatgtggctctggaaggcgtgagccacttcttccgcgaattggccgaggag aagcgcgagggctacgagcgtctcctgaagatgcaaaaccagcgtggcggccgcgctctc ttccaggacatcaagaagccagctgaagatgagtggggtaaaacccagacgccatgaaa gctgccatggccctggagaaaaagctgaaccaggccttttggatcttcatgccctgggt tctgcccgcacggaccccatctctgtgacttcctggagactcacttcctagatgaggaa gtgaagcttatcaagaagatgggtgaccacctgaccaacctccacaggctgggtggcccg gaggctgggctgggcgagtatctcttcgaaaggctcactctcaagcacgactaagagcct tctgagcccagcgacttctgaagggcccttgcaaagtaatagggcttctgcctaagcct

Figure 7B

Amino acid sequence of wildtype FLT (SEQ ID NO: 14)

```
M S S Q I R Q N Y S T D V E A A V N S L
V N L Y L Q A S Y T Y L S L G F Y F D R
D D V A L E G V S H F F R E L A E E K R
E G Y E R L L K M Q N Q R G G R A L F Q
D I K K P A E D E W G K T P D A M K A A
M A L E K K L N Q A L D L H A L G S A
R T D P H L C D F L E T H F L D E E V K
L I K K M G D H L T N L H R L G G P E A
G L G E Y L F E R L T L K H D
```

Figure 8A-B
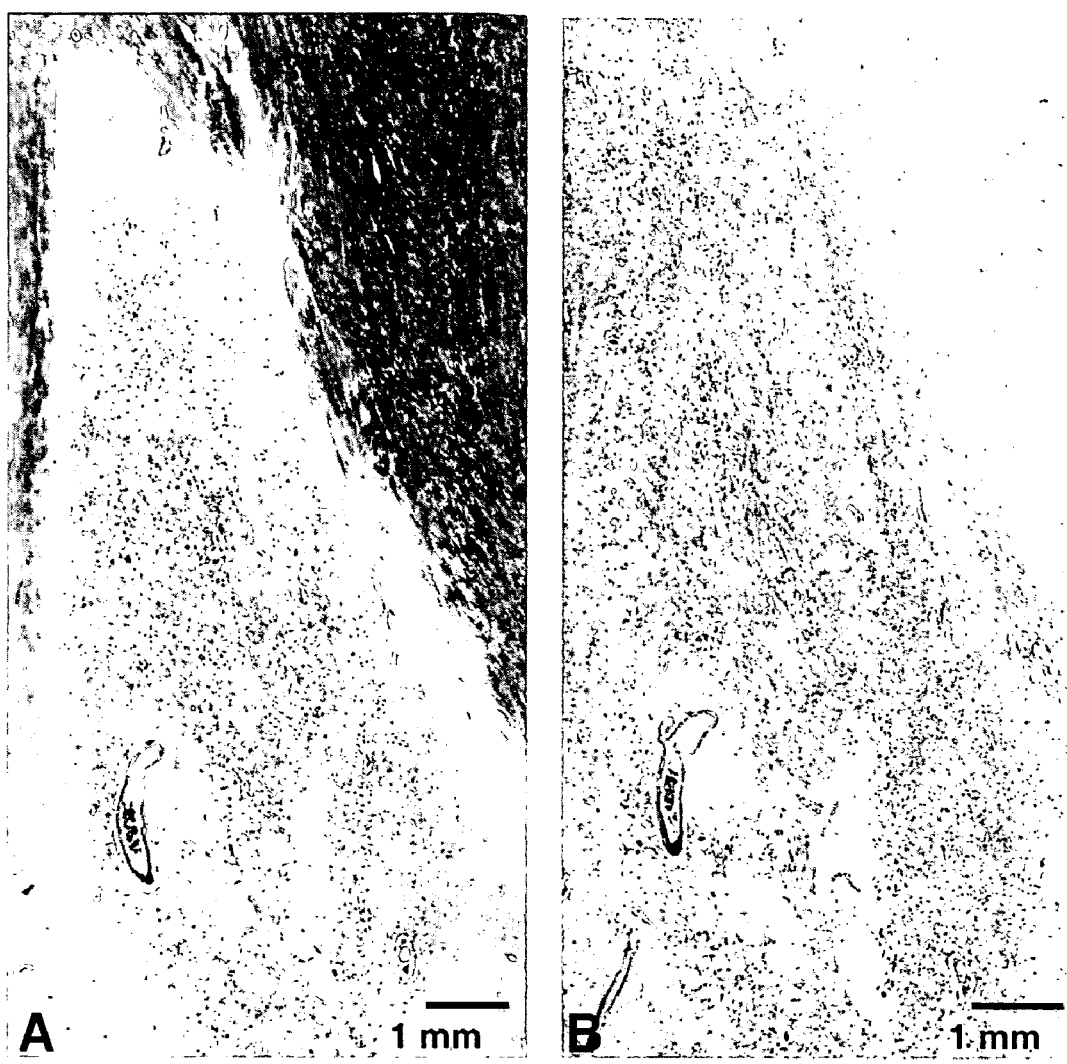

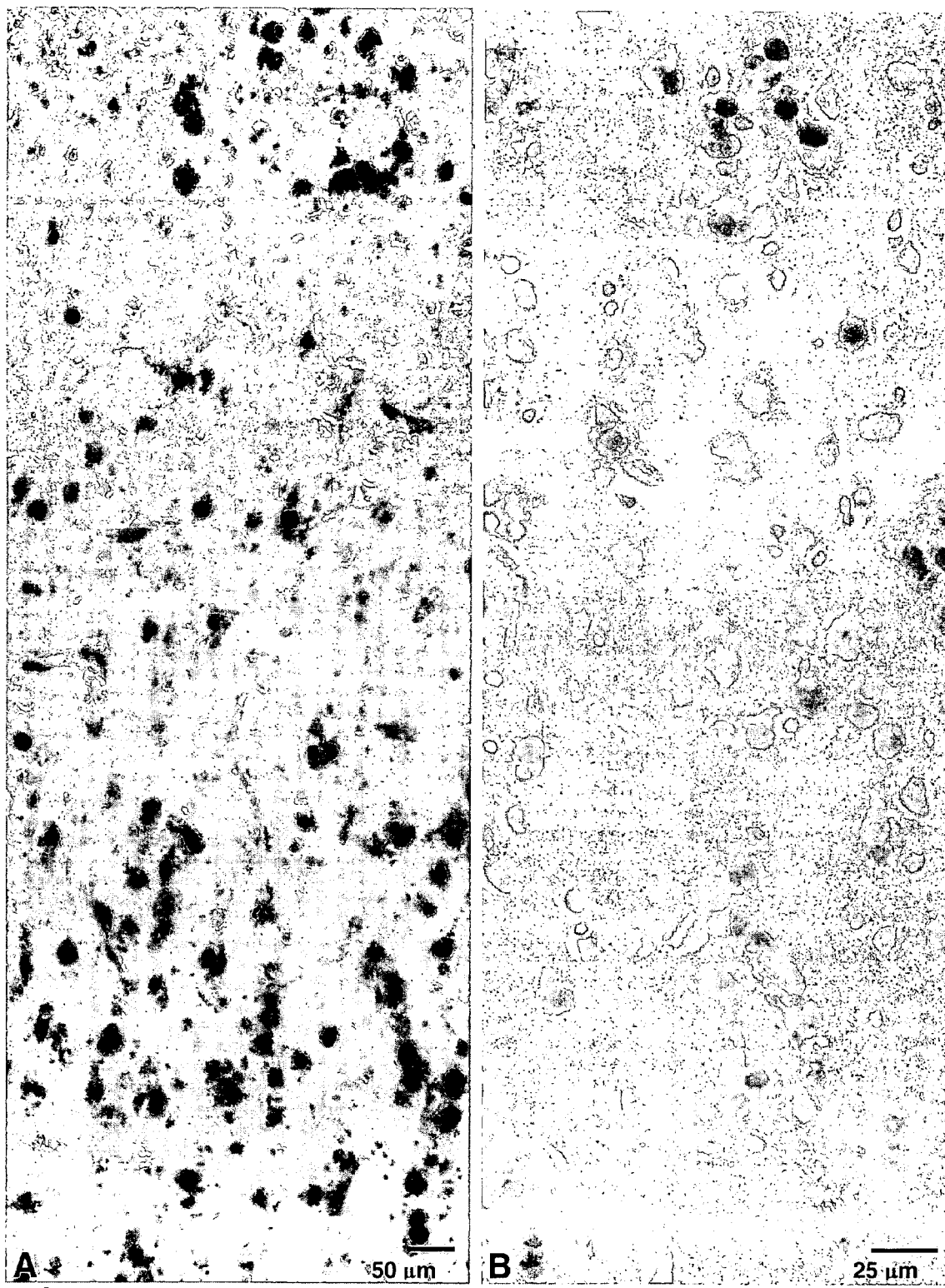
Figure 9A-B

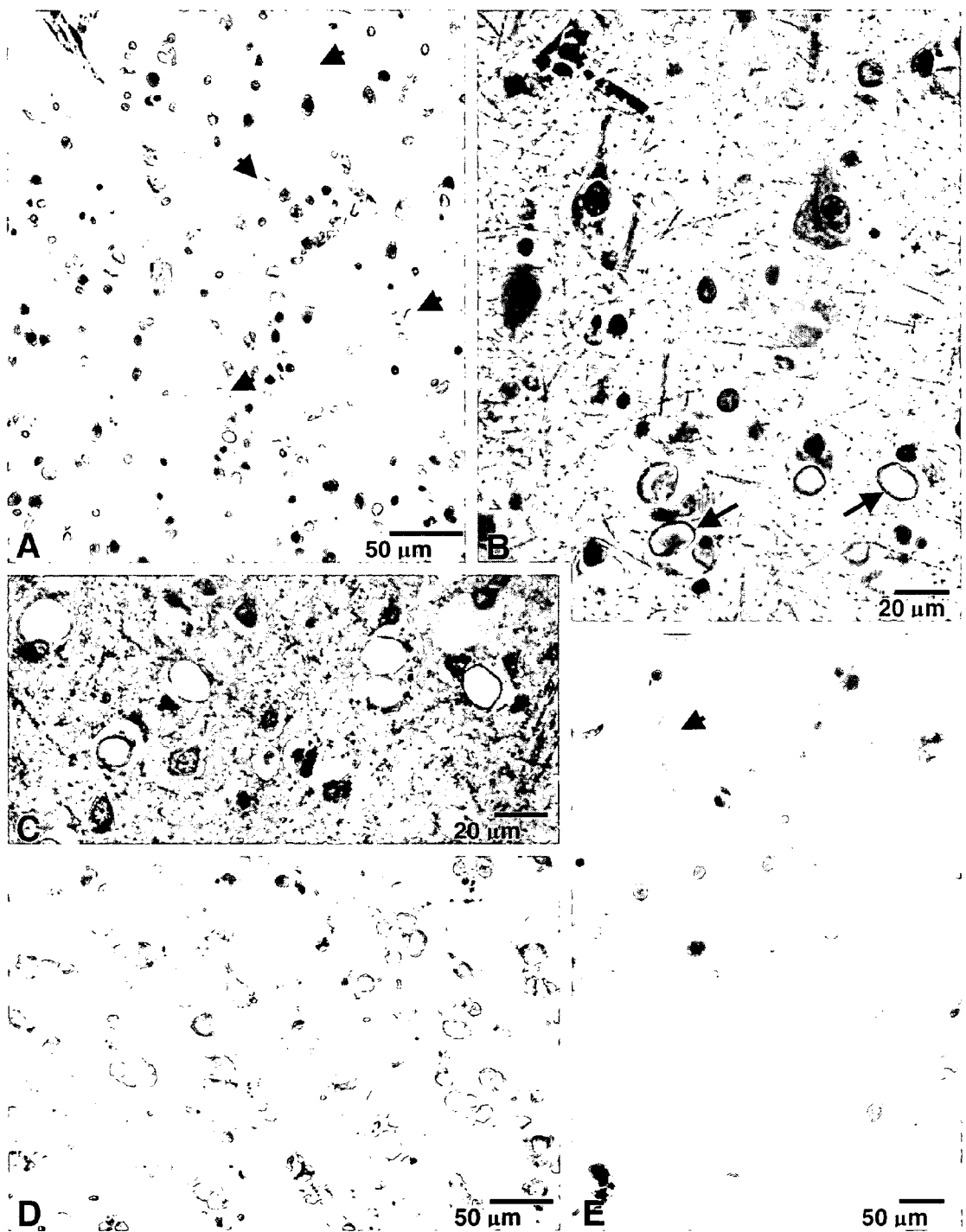
Figure 10A-E

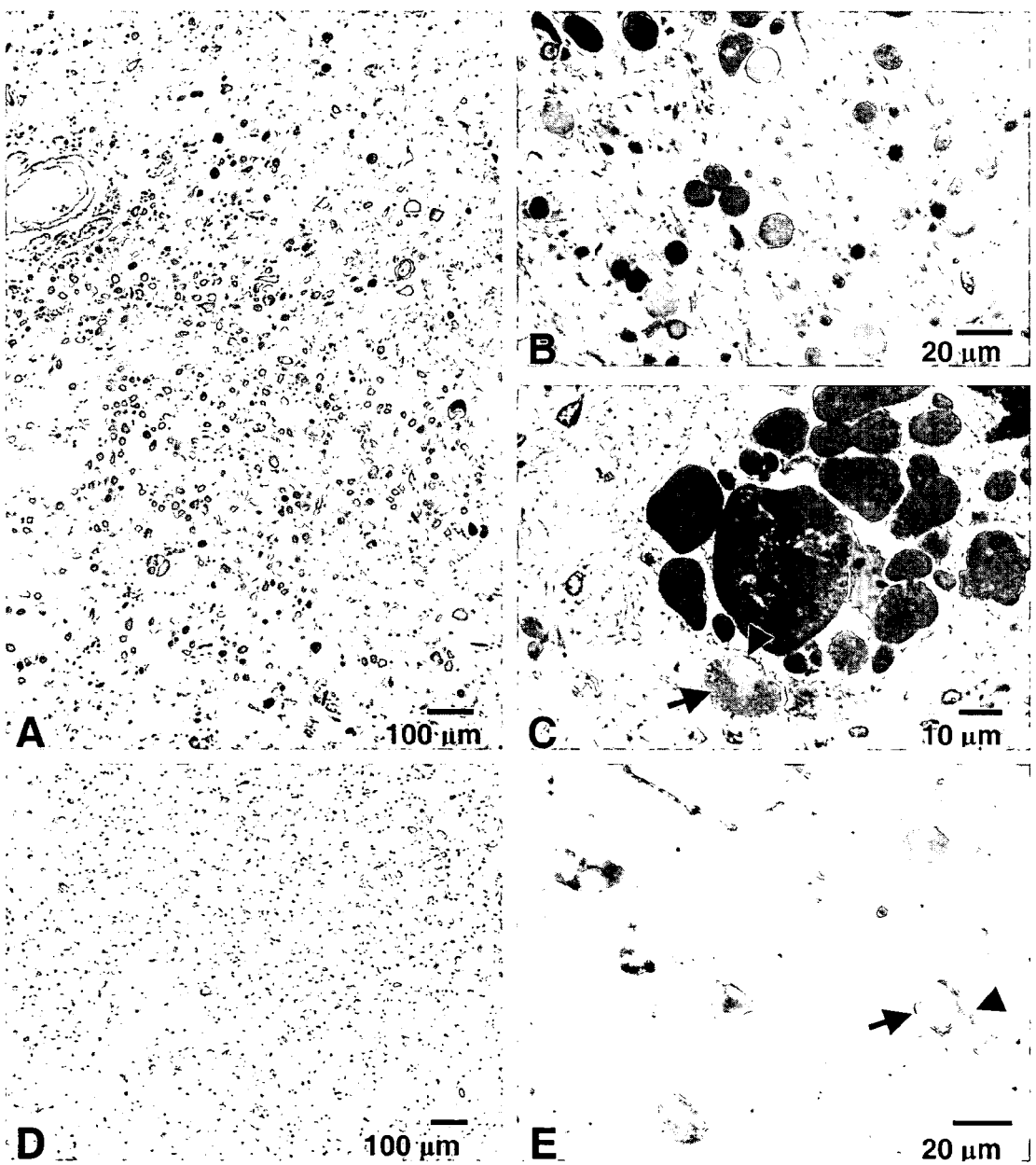
Figure 11A-E

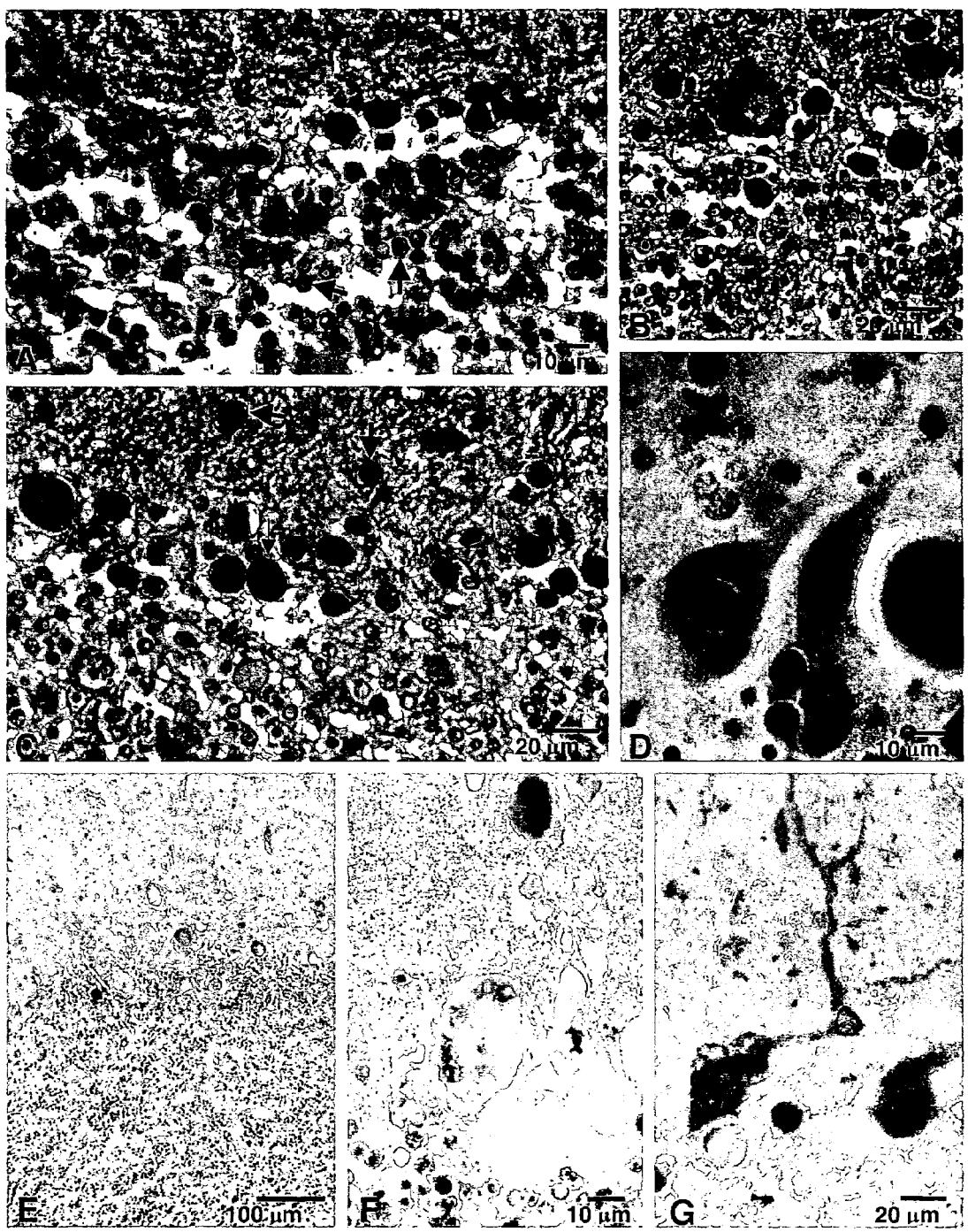
Figure 12A-G

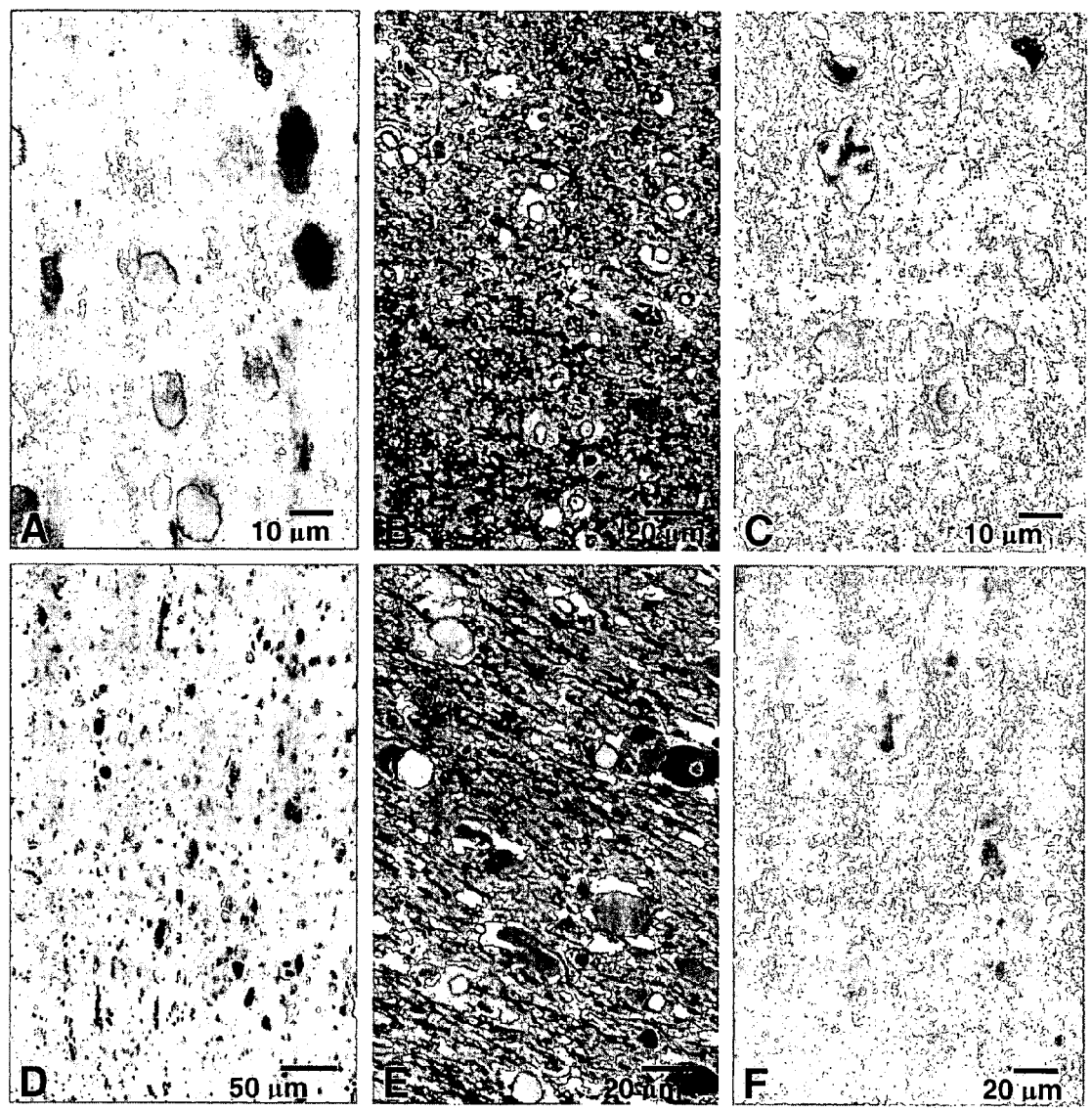
Figure 13A-F

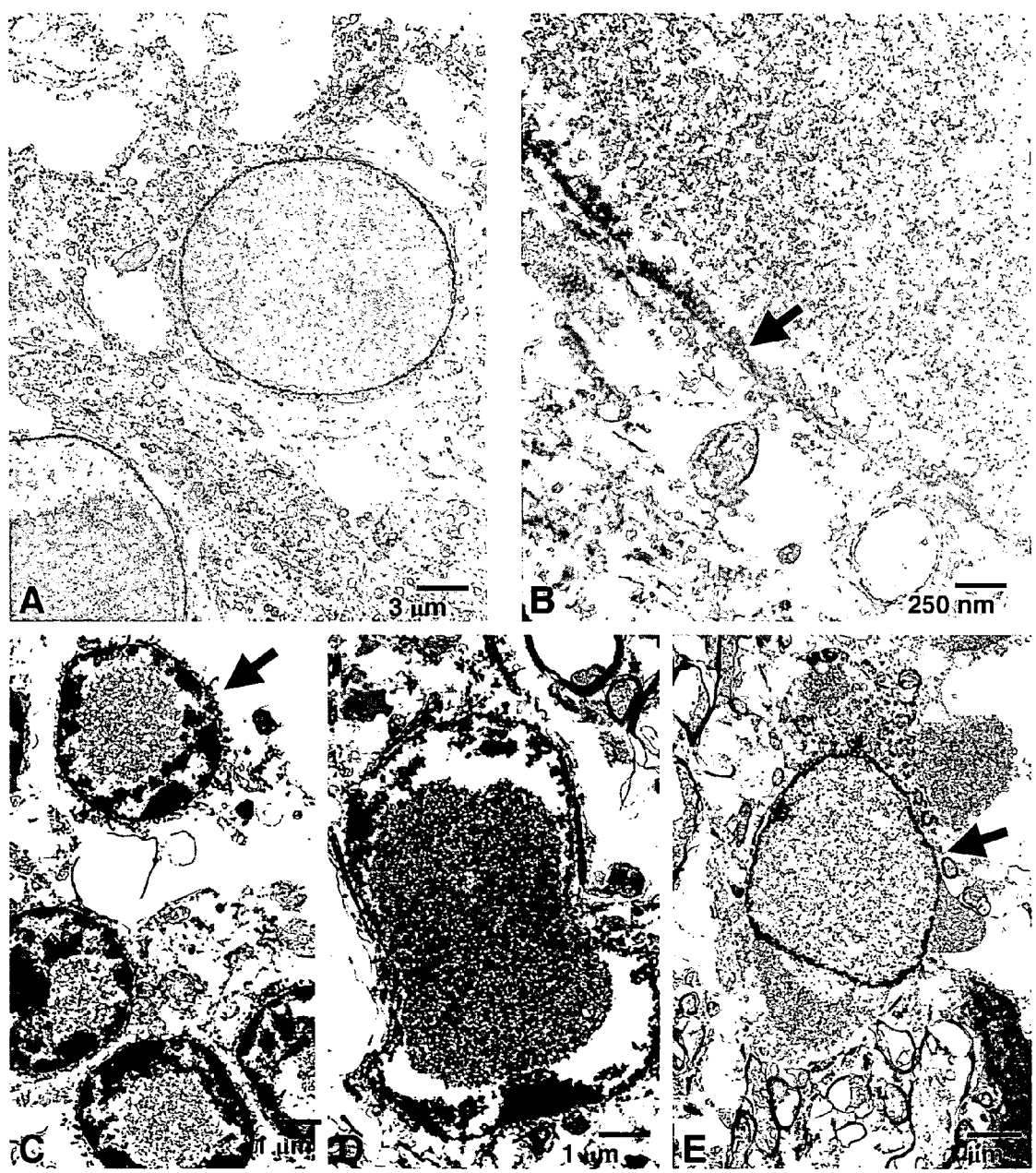
Figure 14A-E

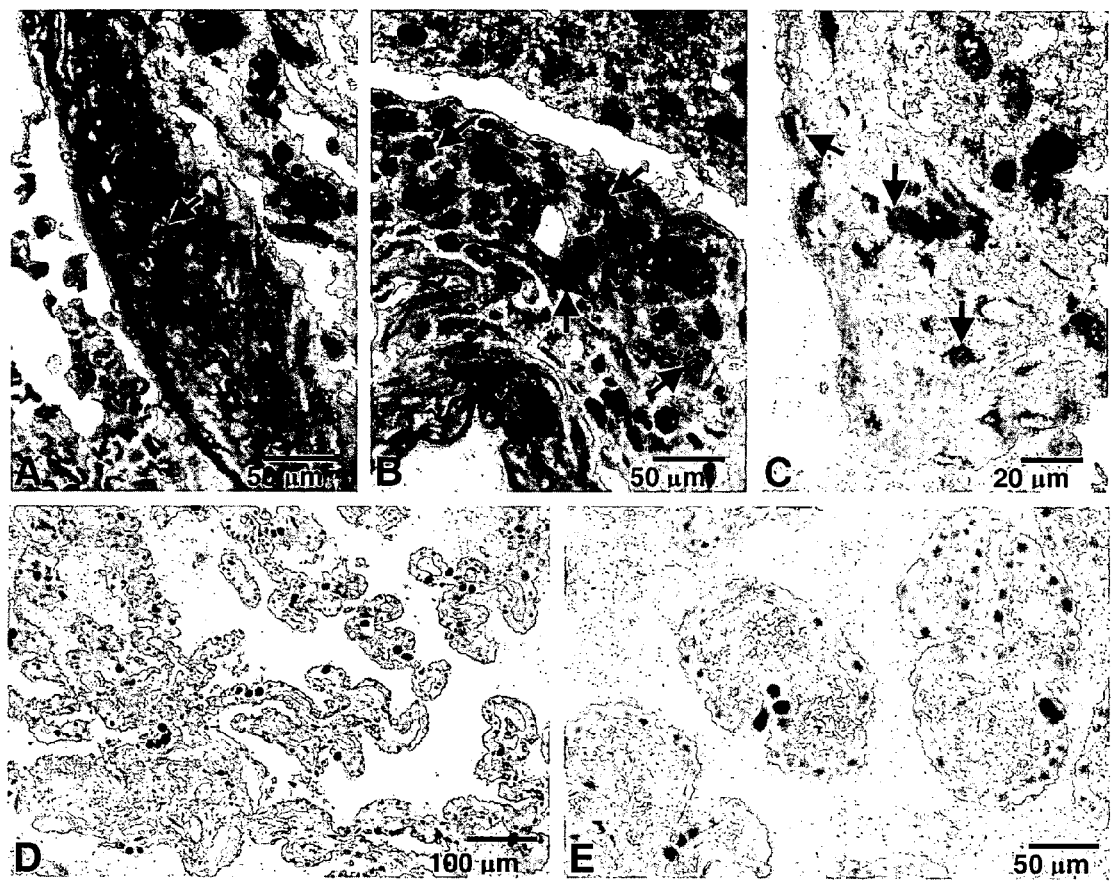
Figure 15A-E

Figure 16A-D

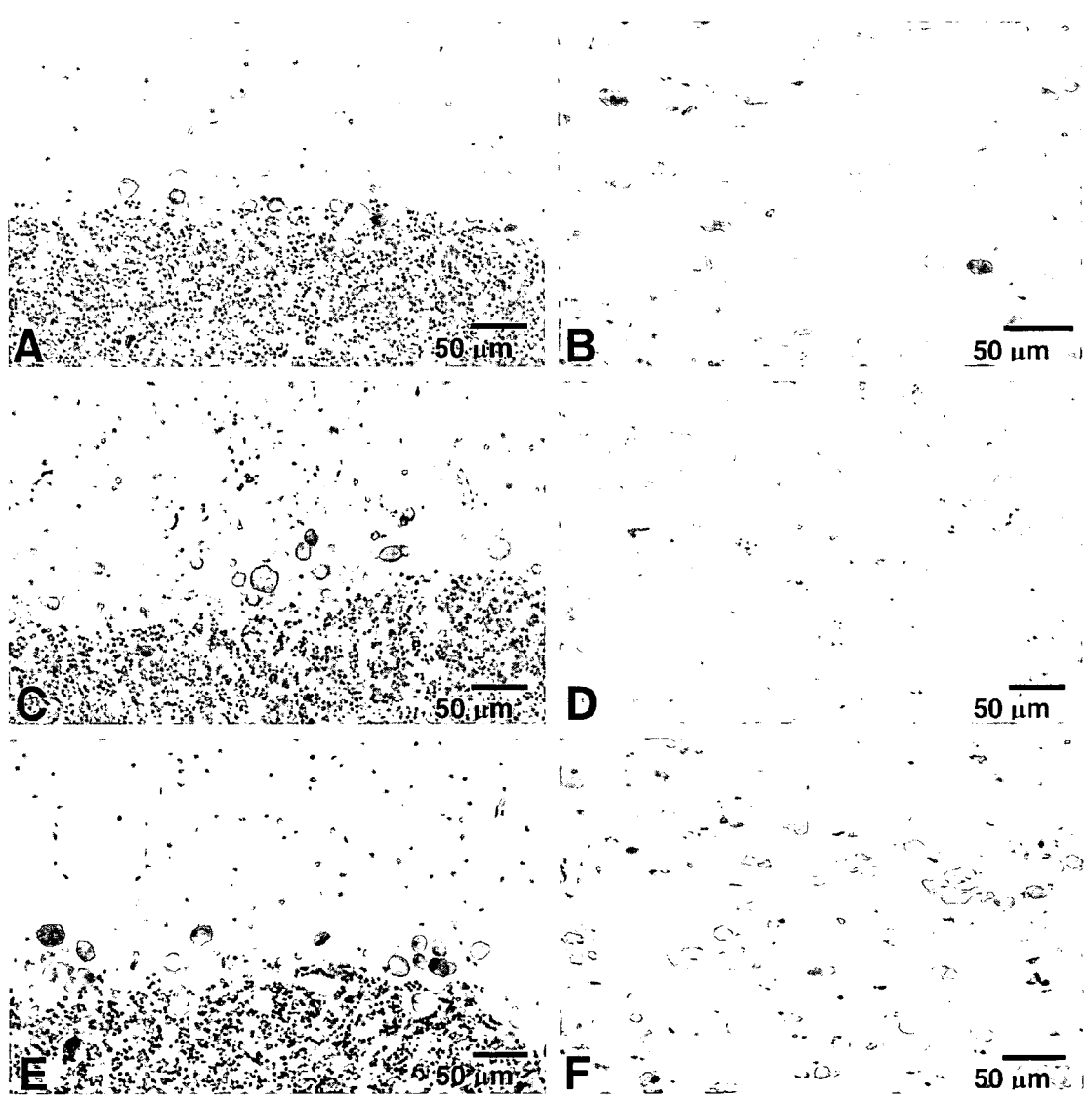
Figure 17A-F

FERRITIN LIGHT SUBUNIT VARIANT-ENCODING NUCLEIC ACIDS, POLYPEPTIDES, TRANSGENIC ANIMALS COMPRISING THE SAME, ANTIBODIES THERETO, AND METHODS OF USE THEREOF

This application claims priority to U.S. Provisional Application 60/418,126, filed Oct. 11, 2002, the entire contents of which are incorporated herein by reference.

Pursuant to 35 U.S.C. §202(c), it is acknowledged that the U.S. Government has certain rights in the invention described, which was made in part with funds from PHS grants P30AG10133 and U01AG16976.

FIELD OF THE INVENTION

This invention relates to the fields of molecular and cellular biology, and neurodegenerative disease. Specifically, nucleic acids encoding a ferritin light chain variant, a ferritin light chain variant polypeptide, ferritin light chain variant polypeptide-specific antibodies, and methods of use thereof are provided.

BACKGROUND OF THE INVENTION

All publications, patent applications, patents, and other references mentioned herein are incorporated by reference in their entirety.

The drug discovery process is currently undergoing a fundamental revolution as it embraces "functional genomics," that is, high throughput genome- or gene-based biology. This approach provides improved means to identify genes and gene products which are associated with or causative of a disease/disorder. The identification of a disease-linked target (e.g., a gene variant) provides a tool with which to diagnose subjects who have the disease or are genetically predisposed to develop the disease. The identification of such disease-linked targets also facilitates the development of therapeutic agents which modulate the activity of these targets and thus provide means to ameliorate and/or treat the disease. Such therapeutic agents may also be used as prophylactic agents to delay and/or prevent the onset of disease in a subject.

Functional genomics relies heavily on high-throughput DNA sequencing technology and bioinformatics to identify gene sequences of potential interest from the numerous molecular biology databases available. There is, however, a continuing need to identify and characterize additional genes/gene variants and their encoded polypeptides/proteins, as targets for drug discovery.

Ferritin has two major functions: iron detoxification and sequestration and storage of intracellular iron (reviewed in Theil, 1987, Annu Rev Biochem. 56:289-315). The mammalian form of this molecule, a protein of ~450 kDa, contains two smaller subunits, designated ferritin heavy polypeptide (FTH1) and ferritin light polypeptide (FTL). The genes encoding FTH1 and FTL have been mapped to human chromosomes 11q12q13 and 19q13.3-13.4, respectively. A functional ferritin molecule is comprised of twenty-four FTH1 and FTL subunits which form a soluble, hollow sphere. The mineral ferrihydite core of the sphere is able to store up to 4,500 atoms of iron. The FTH1 and FTL subunits are thought to have complementary functions with regard to iron storage. The FTH1 subunit possesses a specific ferroxidase activity following rapid uptake of iron and the FTL subunit is considered important for the initiation and stabilization of the ferritin-iron core (Harrison and Arosio, 1996, Biochim Biophys Acta. 1275:161-203).

Proteins which function in iron metabolism underlie several genetic disorders (reviewed in Sheth and Brittenham, 2000, Annu Rev Med. 51:443-64), including some neurodegenerative syndromes. Many of the neurodegenerative syndromes are characterized by extensive intracellular iron accumulation which leads to neuronal dysfunction and toxicity.

SUMMARY OF THE INVENTION

The invention is based on the discovery that a polymorphism within the ferritin L subunit (FTL) gene is associated with a novel, autosomal dominant, neurodegenerative disease characterized by accumulation of ferritin and iron in the form of intracytoplasmic and intranuclear inclusions. Clinically this condition is characterized by tremor, cerebellar signs, extrapyramidal and pyramidal signs, behavioral disturbances and cognitive dysfunction. This symptomatology appears gradually over a period of four decades. The methods described herein allow assessment of a patient with a disease associated with a defect in iron metabolism and/or storage (e.g., a neurodegenerative disease), leading to a more accurate diagnosis and new avenues of therapy.

The invention features an isolated nucleic acid molecule encoding a full length FTL protein variant, which is associated with a neurodegenerative disease (e.g. SEQ ID NO:1). The invention also encompasses the nucleic acid sequence of the FTL exon which comprises the region of divergence of the variant FTL gene described herein (e.g. SEQ ID NO:3). The gene variant of the present invention comprises a 2-bp thymine (T) cytosine (C) duplication/insertion mutation between nucleotides 498 and 499, which is located within exon 4 of the wild type FTL gene. Thus the FTL variant nucleic acid molecule encompasses both SEQ ID NO:1 or 3.

The invention also features an isolated polypeptide which is associated with a neurodegenerative disease. The polypeptide variant of the present invention differs from the wild-type FTL at amino acids 167 to 175 and has an additional 16 amino acids in positions 176 to 191. In one embodiment, the polypeptide variant has the amino acid sequence of SEQ ID NO:2.

Also provided are antibodies which are immunologically specific for the FTL variant of the present invention. These FTL variant specific antibodies may be used to advantage to detect the presence of a FTL variant polypeptide or fragment thereof in a sample.

Oligonucleotide primers are also described herein. Such oligonucleotide primers comprise nucleic acid sequences that may be used to advantage in the methods of the invention. Such methods include polymerase chain reaction (PCR) assays, for example, to amplify a region of a FTL gene variant. Such PCR-based methods enable the detection of a FTL gene variant in a sample derived from a patient. Since the presence of a FTL gene variant of the present invention is associated with a predisposition of an individual to a neurodegenerative disease, detection of such a variant provides a tool with which to predict the onset of a neurodegenerative disease in the individual. Moreover, such methods may also be used to diagnose a patient exhibiting neurological symptoms with a FTL variant related disease. The primer can be about 14 to about 30 nucleotides in length. In one embodiment the oligonucleotide is 10-30 bp in length. The nucleic acid primer may include a nucleotide sequence selected from the group consisting of SEQ ID NOs: 6-11.

The invention also features a method for characterizing a patient diagnosed with a neurodegenerative disease. The method includes determining if the patient has a neurodegenerative disease and then assessing said patient for the presence or absence of an FTL variant. The neurodegenerative disease may be characterized initially by tremors and later progress to varying degrees of behavioral disturbances, ataxia, dyarthria, and cognitive decline. Characterizing the patient can include identifying a treatment regimen suitable for the patient based, at least in part, on the presence or absence of the variant in the patient. FTL gene variants can include, for example, the insertion of a thymine and cytosine between nucleotide positions 498 and 499 which results in a variant FTL polypeptide having an altered carboxy terminus.

The invention also features a method for diagnosing or determining a predisposition for a neurodegenerative disease in a patient based on the presence or absence of the FTL gene variant. In one embodiment, the variant comprises SEQ ID NO:1 or 3.

In yet another embodiment, the invention features a transgenic animal comprising a ferritin light chain gene variant of SEQ ID NO: 1 or a functional fragment thereof.

The invention also features a kit for practicing the method described above. The kit may include an antibody which is immunologically specific for the FTL variant of the present invention, and/or oligonucleotide primers useful for detecting and/or amplifying nucleic acids encoding the FTL variant of the present invention. In one embodiment, the FTL variant of the invention is an FTL nucleic acid having a TC insertion between bp 498 and 499, or the protein encoded thereby. The kit may optionally comprise a solid support and instructions for use.

Unless otherwise defined, all technical and scientific terms used herein have the same meaning as commonly understood by one of ordinary skill in the art to which this invention pertains. The materials, methods, and examples are illustrative only and not intended to be limiting.

Other features and advantages of the invention will be apparent from the following detailed description, example, and claims.

DETAILED DESCRIPTION OF THE DRAWINGS

FIG. 1 shows a pedigree of "family L". Affected individuals are shown by the filled symbols ○ and □. Open symbols represent unaffected individuals. The symbol □ represents nine unaffected individuals. The proband is indicated by the arrow. Deceased members are indicated by /. Genetic analysis was performed on individuals II-3, II-5, III-11, III-12, III-22 to 27, IV-6 and IV-11. Biopsy studies were performed on the proband (III-12) and individuals III-11, III-17 and IV.

FIGS. 2A-D depict the purification and characterization of the ferritin inclusions. (A) H& E-stained preparation of post-detergent treated pellet. (B) Electron micrograph showing the contents of the isolated inclusions. (C) Tris-Tricine SDS-PAGE of the inclusion proteins isolated from cerebellum (lane 3) and putamen (lane 4). The ~22 KDa band (lane 3) was subjected to Edman n-terminal amino acid sequence analysis. Inclusions isolated from the cerebellum of a normal control did not show any bands (lane 2). Lane 5 shows a western blot of lane 3 probed with antibodies immunologically specific for ferritin. Lane 1: Low molecular-mass markers (Amersham) in KDa. (D) Mass/charge ratio (m/z) in MALDI-MS of the proteins isolated from the inclusions.

FIGS. 3A-E show results from sequencing analyses of wild type and variant FTL genes. (A) Direct DNA sequencing of exon four of the FTL gene shows the presence of the wild-type sequence (top) and a mutant sequence (bottom) having a 2-bp duplication (underlined). (B) Cloning of the mutant allele shows the presence of the duplication insertion. (C)Nucleotide and translated amino acid sequence of the C-terminal portions of wild-type (175 amino acids) and mutant (191 amino acids) FTL. The 2-bp insertion in the mutant FTL cDNA is in italics and underlined. The new C-terminal amino acid sequence in the mutant FTL sequence is also underlined. (D) Analysis of ferritin expression by RT-PCR shows the presence of a band of 727 bp corresponding to full-length FTL cDNA (lane 4). Cloning and sequencing of this band showed the presence of both, wild-type and mutant alleles. RNA pretreated with RNase A showed no amplification (lane 3). As a positive control, RT-PCR for GAPD is shown in lane 2. 123 molecular mass marker (Gibco) was run on lane 1 and Hind III digestion of Lambda DNA (Gibco) was run on lane 6. (E) Western blot analysis using antibodies 1277 (specific for wild-type FTL) and 1283 (specific for mutant FTL). Lanes 1 and 4 were loaded with recombinant FTH1. Lanes 2 and 5 were loaded with recombinant FTL. Lanes 3 and 6 were loaded with a preparation of bodies isolated from the cerebellum of the proband. Lanes 1-3 were tested with antibody 1277. Lanes 4-6 were tested with antibody 1283.

FIG. 4 shows a nucleic acid sequence of the FTL variant cDNA (SEQ ID NO: 1).

FIG. 5 shows an amino acid sequence of the FTL variant polypeptide (SEQ ID NO: 2) encoded by SEQ ID NO: 1.

FIG. 6 shows a fragment of exon 4 encoding the FTL variant (SEQ ID NO: 3).

Figure 1:
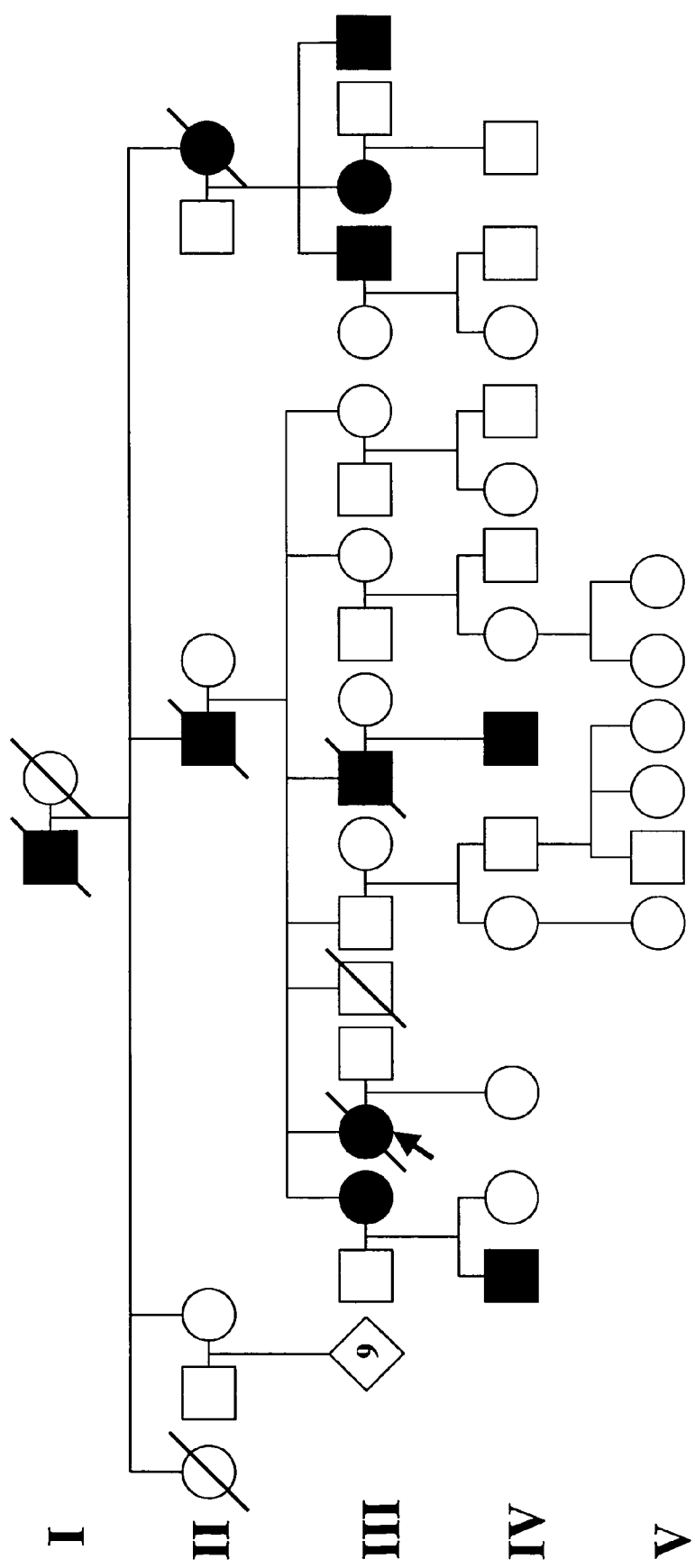

FIGS. 7A and B show a nucleic acid sequence (SEQ ID NO: 13) and an amino acid sequence (SEQ ID NO: 14) of a wildtype FTL cDNA.

FIG. 8A-B show sections of the proband's putamen stained with Heidenhain-Woelcke method (A) and with Pearls method (B). Note the severe cavitation (A and B) and the accumulation of numerous iron containing bodies in the putamen (B).

FIG. 9A-B show sections of the proband's frontal cortex. Immunolabeling with an antibody to human ferritin (A) and staining with Pearls' method for iron (B). Nuclei of glial cells in cortical layers II to VI contain ferritin bodies of different sizes. A diffuse ferritin immunoreactivity is also noted in the cytoplasm (A). Pearls stain is strong in the nuclei of glial cells and weak in the cytoplasm (B).

FIGS. 10A-E show sections of the proband's neocortex. Staining with H&E (A), Bodian (B) and toluidine blue (C). Immunohistochemistry using an antibody against ferritin (D-E). Intranuclear bodies are faintly stained (A, C) and are not argentophylic (arrows) (B). Numerous ferritin immunoreactive bodies are seen (D). Ferritin immunoreactive bodies are mostly seen in nuclei of glial cells, including satellite cells, and associated to vascular structures (arrow) (E).

FIGS. 11A-E show sections of the proband's putamen. Staining with H&E (A) and toluidine blue (B, C). Immunohistochemistry using an antibody against ferritin (D-E). Note that bodies may vary in size and shape (A-C). Bodies may be intranuclear (arrowhead) and/or intracytoplasmic (arrow) (C). When large masses are seen, it is not possible to determine whether they derive from intra- or extracellular bodies. Bodies immunoreact with ferritin antibodies (D-E).

The localization of ferritin bodies in astrocytes is evident in double immunohistochemical preparations using antibodies against ferritin (red) and GFAP (brown). Note the GFAP immunoreactivity in the cytoplasm (arrowhead) and cell processes and the ferritin immunoreactivity in the nucleus (arrow) (E). In some instances, ferritin immunoreactivity is also seen in the cytoplasm.

FIGS. 12A-G show sections of the proband's cerebellum. Staining with toluidine blue (A-C) and H&E (D). Immunohistochemistry using an antibody against ferritin (E-G). Thick arrows indicate intranuclear bodies in granule cells (A) and in cells of the molecular layer (C). Note the presence of intranuclear bodies (thin arrow) at the junction between the granular cell layer and the molecular cell layer (C). These bodies are most likely within Golgi epithelial cells. Absence of Purkinje cells is conspicuous (A, C). Purkinje cells without bodies are rarely seen (B). Purkinje cells contain intranuclear and/or cytoplasmic bodies that appear strongly eosinophilic (D). Ferritin immunoreactive bodies are present in all layers of the cerebellar cortex (E-G). In double immunohistochemical preparations, Purkinje cells perikarya and dendrites are immunolabeled with an antibody against calcium binding protein (brown). Intranuclear and intracytoplasmic bodies are labeled using an antibody against ferritin (red). Note the presence of bodies within the dendritic cytoplasm.

FIGS. 13A-F show sections of the proband's cerebral and cerebellar white matter. Staining with H&E (A, D) and toluidine blue (B, E). Immunohistochemistry using an antibody against ferritin (C, F). Numerous intranuclear bodies with variable degree of eosinophilia are present in glial cells of the white matter (A, D). The size of the intranuclear bodies differs in the cerebral (B) versus cerebellar white matter (E). Anti-ferritin immunoreactivity varies in its intensity between nuclei and cytoplasms of glial cells (C, F).

FIGS. 14A-E show sections of the proband's putamen (A, B) and cerebellum (C-E). Electron micrograph showing two nuclei each containing an intranuclear body (A). The intranuclear bodies are composed of granular material (A-E) that has a varying degree of electron density. Note that the chromatin (arrow) accumulates toward the nuclear membrane (B). The nuclei of the cerebellar granule cells (arrow) contain deposits of various sizes (C). A glial cell of the cerebellar white matter contains an electron dense intranuclear body (D). A glial cell (arrow) contains intranuclear and intracytoplasmic granular material (E).

FIGS. 15A-E show blood vessels stained with toluidine blue (A-C). Choroid plexuses immunolabeled using an antibody against ferritin (D) and stained with Pearls' method for iron (E). Intranuclear bodies are present in cells of the walls of arteries (A, B) and veins (C). Note the presence of intranuclear bodies (arrow) within cells of the tunica media (A) and tunica adventitia (B) in arteries in the putamen. In addition, cells of a wall of a vein, including endothelial cells, show the presence of intranuclear bodies (arrows). Cells of the choroidal epithelium contain intranuclear bodies that are immunopositive for ferritin (D) and stained for ferric iron (E).

FIGS. 16A-D show skin biopsies of individual IV-6 (A-C) and renal biopsy of individual III-17 (D). Intranuclear inclusions (arrow) are seen in fibroblasts from the papillary dermis (A-C). Section stained with toluidine blue (A), electron micrograph (B) and section immunolabeled with anti-ferritin antibodies (C). Intranuclear (thick arrow) and intracytoplasmic (thin arrow) ferritin immunoreactivity is seen in cells of the renal tubular epithelium (D).

FIGS. 17A-F show sections of the proband's cerebellar cortex (A, C, E) and cerebellar white matter (B,D,F). Immunohistochemistry using an antibody against wild-type FTL (Ab 1277) (A, B), an antibody specific for the mutant FTL (Ab 1283) (C, D), and an antibody against FTH1 (Y-16) (E, F). Intranuclear and intracytoplasmic immunopositivity is seen with all three antibodies.

DETAILED DESCRIPTION OF THE INVENTION

The present invention is directed to the identification of a novel genetic defect in the ferritin light chain gene, which is associated with the development of a neurodegenerative disease characterized by aberrant deposition of ferritin and iron in the cells of the central nervous system (CNS). The invention provides an isolated nucleic acid sequence of the FTL gene variant, which diverges from that of the wild type ferritin light chain gene due to the presence of a two nucleotide duplication/insertion after nucleotide 498. The duplication produces a FTL variant polypeptide having an extended carboxy terminus, wherein an amino acid other than phenylalanine is encoded by codon 167 and subsequent amino acids diverge from those of wild type FTL. Also provided are methods for diagnosing or predicting a predisposition to a neurodegenerative disease, comprising detecting in a sample from a subject the presence of a mutation at a nucleotide position corresponding to codon 167 of ferritin light chain or a fragment thereof, the presence of a mutation indicating the presence of or a predisposition to the neurodegenerative disease. Methods for diagnosing or predicting a predisposition to a neurodegenerative disease also comprise detecting in a sample from a subject the presence of a variant ferritin light chain having an extended carboxy terminus, which provides a clinical indicator of a neurodegenerative disease or a predisposition to such a condition.

I. Definitions:

Various terms relating to the biological molecules of the present invention are used hereinabove and also throughout the specifications and claims.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "promoter region" refers to the transcriptional regulatory regions of a gene, which may be found at the 5' or 3' side of the coding region, or within the coding region, or within introns.

The term "vector" refers to a small carrier DNA molecule into which a DNA sequence can be inserted for introduction into a host cell where it will be replicated. An "expression vector" is a specialized vector that contains a gene with the necessary regulatory regions needed for expression in a host cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel characteristics of the sequence.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', $F(ab')_2$ and F(v).

With respect to antibodies of the invention, the term "immunologically specific" refers to antibodies that bind to one or more epitopes of a protein of interest (e.g., a FTL variant), but which do not substantially recognize and bind other molecules in a sample containing a mixed population of antigenic biological molecules.

As used herein, the terms "reporter," "reporter system", "reporter gene," or "reporter gene product" shall mean an operative genetic system in which a nucleic acid comprises a gene that encodes a product which when expressed produces a reporter signal that is readily measurable, e.g., by biological assay, immunoassay, radioimmunoassay, or by calorimetric, fluorogenic, chemiluminescent or other method. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, and may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like. The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on to or inherited by progeny cells or organisms of the recipient cell or organism. In other applications, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide. An exemplary oligonucleotide can consist of any number of nucleotides between 10 and 100.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and the method used. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "percent identical" is used herein with reference to comparisons among nucleic acid or amino acid sequences. Nucleic acid and amino acid sequences are often compared using computer programs that align sequences of nucleic or amino acids thus defining the differences between the two. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (at http://www.ncbi.nlm.nih.gov/blast/; Altschul et al., 1990, J Mol Biol 215:403-410) using a gapped alignment with default parameters, may be used to determine the level of identity and similarity between nucleic acid sequences and amino acid sequences.

The present invention also includes active portions, fragments, and derivatives of the FTL variant polypeptide of the invention. An "active portion" of a FTL variant protein or polypeptide means a peptide which is less than said full length FTL variant polypeptide, but which retains its essential biological activity, e.g., causes neurodegenerative disease.

An exemplary active portion, fragment, or derivative of a FTL variant comprises the unique amino acid sequence of the carboxy terminus of the full length FTL variant. The unique carboxy terminus diverges from that of the wild type ferritin light chain at the amino acid residue encoded by codon 167 and spans those amino acid sequences encoded by codons 167-191.

A "fragment" of FTL variant polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. Fragments of FTL variant polypeptide sequence, antigenic determinants, or epitopes are useful for raising antibodies to this portion of the FTL variant protein amino acid sequence.

A "derivative" of FTL variant polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, without fundamentally altering the essential activity of the FTL variant polypeptide.

As mentioned above, the FTL variant polypeptide or protein of the invention includes any analogue, fragment, derivative or mutant which is derived from the FTL variant, comprises the unique carboxy terminus of the FTL variant, and which retains at least one property or other characteristic of the FTL variant. Different "variants" of the FTL variant polypeptide may exist in nature. These variants may be alleles characterized by differences in the nucleotide sequences of the gene coding for the protein, or may involve different RNA processing or post-translational modifications. The skilled person can produce variants having single or multiple amino acid substitutions, deletions, additions or replacements. These variants may include inter alia: (a) variants in which one or more amino acid residues are substituted with conservative or non-conservative amino acids, (b) variants in which one or more amino acids are added to the FTL variant, (c) variants in which one or more amino acids include a substituent group, and (d) variants in which the FTL variant is fused with another peptide or polypeptide such as a fusion partner, a protein tag or other chemical moiety, that may confer useful properties to a FTL variant, such as, for example, an epitope for an antibody, a polyhistidine sequence, a biotin moiety and the like. Other FTL variant-like proteins of the invention include variants in which amino acid residues from one species are substituted for the corresponding residue in another species, either at the conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to the person having ordinary skill in the art.

To the extent such allelic variations, analogues, fragments, derivatives, mutants, and modifications, including alternative nucleic acid processing forms and alternative post-translational modification forms result in derivatives of the FTL variant that retain any of the biological properties of the FTL variant, they are included within the scope of this invention.

The term "functional" as used herein implies that the nucleic or amino acid sequence is functional for the recited assay or purpose.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a larger molecule. In embodiments in which the specific binding pair are nucleic acid sequences, they will be of a length to hybridize to each other under conditions of the assay, preferably greater than 10 nucleotides long, more preferably greater than 15 or 20 nucleotides long.

As used herein, the terms "ferritin light chain variant", "ferritin light subunit variant", "FTL gene variant", "FTL variant gene", or "FTL variant" refer to a mutant variant of FTL having a 2-bp duplication insertion mutation in exon 4 of the wild type ferritin light chain gene (FTL). The mutation caused a frameshift alteration that resulted in the generation of an elongated FTL variant protein.

As used herein, "codon 167" refers to the codon (i.e., the tri-nucleotide sequence) that encodes the $167^{th}$ amino acid position in a ferritin light chain.

As used herein, the term "agent" denotes a chemical compound, a mixture of chemical compounds, a biological macromolecule, or an extract made from biological materials such as bacteria, plants, fungi, or animal (particularly mammalian) cells or tissues. Agents are evaluated for potential biological activity by inclusion in screening assays described hereinbelow.

II. Preparation of FTL Variant-Encoding Nucleic Acid Molecules, FTL Variant Polypeptides, and Antibodies Thereto

A. Nucleic Acid Molecules

Nucleic acid molecules encoding the FTL variant polypeptide of the invention may be prepared by two general methods: (1) Synthesis from appropriate nucleotide triphosphates, or (2) Isolation from biological sources. Both methods utilize protocols well known in the art.

The availability of nucleotide sequence information, such as a full length nucleic acid sequence having SEQ ID NO: 1 (FIG. 4), enables preparation of isolated nucleic acid molecules of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 1.4 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 1.4 kb double-stranded molecule. A synthetic DNA molecule so constructed may then be cloned and amplified in an appropriate vector.

Nucleic acid sequences encoding a FTL variant polypeptide may be isolated from appropriate biological sources using methods known in the art. In a preferred embodiment, a cDNA clone is isolated from a cDNA expression library of Homo sapiens (H. sapiens) origin. In an alternative embodiment, utilizing the sequence information provided by the cDNA sequence corresponding to a FTL variant polypeptide, a genomic clone encoding a FTL variant polypeptide may be isolated. Alternatively, cDNA or genomic clones having homology to a FTL variant polypeptide may be isolated from other species, such as other organisms which possess a FTL chain, using oligonucleotide probes corresponding to predetermined sequences within the FTL variant gene.

In accordance with the present invention, nucleic acids having the appropriate level of sequence homology with the protein coding region of SEQ ID NO: 1 may be identified by using hybridization and washing conditions of appropriate stringency. For example, hybridizations may be performed, according to the method of Sambrook et al., (supra) using a hybridization solution comprising: 5×SSC, 5× Denhardt's reagent, 0.5-1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 0.5-1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_m = 81.5° C. + 16.6 \text{Log} [Na+] + 0.41(\% G+C) - 0.63 (\% \text{formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5× Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5× Denhardt's solution, 0.5% SDS and 100 µg/ml denatured salmon sperm DNA at 42° C., and washed in 0.1×SSC and 0.5% SDS at 65° C. for 15 minutes.

Nucleic acids of the present invention may be maintained as DNA in any convenient cloning vector. In a preferred embodiment, clones are maintained in a plasmid cloning/ expression vector, such as pBluescript (Stratagene, La Jolla, Calif.), which is propagated in a suitable E. coli host cell.

Genomic clones of the invention encoding the FTL variant polypeptide may be maintained in lambda phage FIX II (Stratagene).

FTL variant polypeptide-encoding nucleic acid molecules of the invention include cDNA, genomic DNA, RNA, and fragments thereof which may be single- or double-stranded. An exemplary fragment of the FTL variant polypeptide-encoding nucleic acid sequence is exon 4 of the FTL variant gene comprising SEQ ID NO: 3 (FIG. 6). This invention also provides oligonucleotides (sense or antisense strands of DNA or RNA) having sequences capable of hybridizing with at least one sequence of a nucleic acid molecule of the present invention, such as selected segments of the cDNA having SEQ ID NO: 1. Such fragments and oligonucleotides are useful as probes for detecting or isolating FTL variant genes.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

Additionally, the term "substantially complementary" refers to oligo sequences that may not be perfectly matched to a target sequence, but the mismatches do not materially affect the ability of the oligo to hybridize with its target sequence under the conditions described.

Thus, the coding sequence may be that shown in SEQ ID NO: 1 or it may be a mutant, variant, derivative or allele of this sequence. The sequence may differ from that shown by a change which is one or more of addition, insertion, deletion and substitution of one or more nucleotides of the sequence shown. Changes to a nucleotide sequence may result in an amino acid change at the protein level, or not, as determined by the genetic code.

Thus, a nucleic acid according to the present invention may include a sequence different from the sequence shown in SEQ ID NO: 1 yet encode a polypeptide with the same amino acid sequence.

On the other hand, the encoded polypeptide may comprise an amino acid sequence which differs by one or more amino acid residues from the amino acid sequence shown in SEQ ID NO: 2. Nucleic acid encoding a polypeptide which is an amino acid sequence mutant, variant, derivative or allele of the sequence shown in SEQ ID NO: 1 is further provided by the present invention. Nucleic acid encoding such a polypeptide may show greater than 60% homology with the coding sequence shown in SEQ ID NO: 1, greater than about 70% homology, greater than about 80% homology, greater than about 90% homology or greater than about 95% homology.

The present invention provides a method of obtaining nucleic acid of interest, the method including hybridization of a probe having part or all of the sequence shown in SEQ ID NO: 1, or a complementary sequence, to target nucleic acid. Hybridization is generally followed by identification of successful hybridization and isolation of nucleic acid which has hybridized to the probe, which may involve one or more steps of PCR.

Such oligonucleotide probes or primers, as well as the full-length sequence (and mutants, alleles, variants, and derivatives) are useful for identifying variants of FTL variant polypeptide having novel properties such as a modified (e.g., reduce or enhanced) ability to cause a neurodegenerative disease. The conditions of the hybridization can be controlled to minimize non-specific binding, and preferably stringent to moderately stringent hybridization conditions are used. The skilled person is readily able to design such probes, label them and devise suitable conditions for hybridization reactions, assisted by textbooks such as Sambrook et al (1989) and Ausubel et al (1992).

In some preferred embodiments, oligonucleotides according to the present invention that are fragments of the sequence shown in SEQ ID NO: 1 or any allele associated with an ability to cause neurodegenerative disease, are at least about 10 nucleotides in length, more preferably at least 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with determining the presence in a test sample of a sequence indicative of a susceptibility to a disorder involving ferritin and/or iron accumulation (e.g., a neurodegenerative disorder).

B. Proteins

FTL variant polypeptide is a mutant form of FTL associated with a neurodegenerative disease characterized by abnormal intracellular ferritin and iron accumulation. As described herein, the mutant FTL protein was identified as a component of cellular inclusions associated with neurodegenerative disease. Full-length FTL variant polypeptide of the present invention may be prepared in a variety of ways, according to known methods. The protein may be purified from appropriate sources, e.g., transformed bacterial or animal cultured cells or tissues derived from organisms containing FTL variant polypeptide (including, but not restricted to *H. sapiens*), by immunoaffinity purification. However, this is not a preferred method due to the low amount of protein likely to be present in a given cell type at any time. The availability of nucleic acid molecules encoding FTL variant polypeptide enables production of FTL variant polypeptide using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of FTL variant polypeptide may be produced by expression in a suitable prokaryotic or eukaryotic system. For example, part or all of a DNA molecule, such as a nucleic acid sequence having SEQ ID NO: 1 may be inserted into a plasmid vector adapted for expression in a bacterial cell, such as *E. coli*. Alternatively, in a preferred embodiment, fusion proteins comprising FTL variant polypeptide linked to a desired polypeptide can be generated. Such FTL variant polypeptide-tagged fusion proteins are encoded by part or all of a DNA molecule, such as the nucleic acid sequence having SEQ ID NO: 1, ligated in the correct codon frame to a nucleotide sequence encoding a portion or all of a desired polypeptide which is inserted into a plasmid vector adapted for expression in a bacterial cell, such as E. coli, or a eukaryotic cell, such as, but limited to, yeast and mammalian cells. Vectors such as those described herein comprise the regulatory elements necessary for expression of the DNA in the host cell (e.g. E. coli) positioned in such a manner as to permit expression of the DNA in the host cell. Such regulatory elements required for expression include promoter sequences, transcription initiation sequences and, optionally, enhancer sequences.

FTL variant polypeptides, or fusion proteins thereof, produced by gene expression in a recombinant prokaryotic or eukaryotic system may be purified according to methods known in the art. In a preferred embodiment, a commercially available expression/secretion system may be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope, GST or the hemagglutinin epitope. Such methods are commonly used by skilled practitioners.

FTL variant polypeptides, and fusion proteins thereof, of the invention, prepared by the aforementioned methods, may be analyzed according to standard procedures. For example, such proteins may be subjected to amino acid sequence analysis, according to known methods.

As discussed above, a convenient way of producing a polypeptide according to the present invention is to express nucleic acid encoding it, by use of the nucleic acid in an expression system. The use of expression systems has reached an advanced degree of sophistication today.

Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow production of the polypeptide. Polypeptides may also be produced in in vitro systems, such as reticulocyte lysate.

A polypeptide which is an amino acid sequence variant, allele, derivative or mutant of the amino acid sequence shown in SEQ ID NO: 2 may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. Particular amino acid sequence variants may differ from that shown in SEQ ID NO: 2 by insertion, addition, substitution or deletion of 1 amino acid, 2, 3, 4, 5-10, 10-20, 20-30, 30-40, 40-50, 50-100, 100-150, or more than 150 amino acids.

The present invention also provides antibodies capable of immunospecifically binding to proteins of the invention. Polyclonal antibodies directed toward FTL variant polypeptide may be prepared according to standard methods, using full length polypeptides, or fragments thereof, including naturally occurring polypeptides and synthetic peptides. In a preferred embodiment, monoclonal antibodies are prepared, which react immunospecifically with various epitopes of FTL variant polypeptide. Monoclonal antibodies may be prepared according to general methods of Köhler and Milstein, following standard protocols. In a particularly preferred embodiment, antibodies may be generated in response to amino acids encoded by codons 167-191 (or a fragment thereof) of the FTL variant. This region of the FTL variant is unique with regard to other known FTL variants and wild type FTL, and, therefore, may comprise a particularly distinctive spectrum of FTL variant-specific antigenic epitopes. Polyclonal and/or monoclonal antibodies may be prepared as described in several laboratory protocol handbooks, including: Molecular Cloning: A Laboratory Manual, Sambrook et al. eds., Cold Spring Harbor Laboratory Press (1989); Ausubel et al. (supra), and Antibodies: A Laboratory Manual, Harlow and Lane eds., Cold Spring Harbor Laboratory Press (1988). Polyclonal or monoclonal antibodies that immunospecifically interact with FTL variant polypeptide may be utilized for identifying and purifying FTL variant protein. For example, antibodies may be utilized for affinity separation of proteins with which they immunospecifically interact. Antibodies may also be used to immunoprecipitate proteins from a sample containing a mixture of proteins and other biological molecules. Other uses of anti-FTL variant polypeptide antibodies are described below.

Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope.

Exemplary antibody fragments, capable of binding an antigen or other binding partner, are Fab fragment consisting of the VL, VH, C1 and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

III. Uses of FTL Variant Polypeptide-Encoding Nucleic Acids, Protein and Antibodies Thereto FTL variant nucleic acids, protein and antibodies thereto, according to this invention, may be used, for example, as research tools to examine the role of FTL in the development of neurodegenerative disease, identify binding partners of FTL variant polypeptide, identify signaling pathways which regulate FTL variant expression, and screen for and characterize agents capable of modulating FTL variant activity.

A. FTL Variant-Encoding Nucleic Acids

FTL variant polypeptide-encoding nucleic acids may be used for a variety of purposes in accordance with the present invention. FTL variant polypeptide-encoding DNA, RNA, or fragments thereof may be used as probes to detect the presence of and/or expression of genes encoding FTL variant-like proteins in different species and define tissue specific expression patterns in such species. Methods in which FTL variant polypeptide-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The FTL variant polypeptide-encoding nucleic acids of the invention may also be utilized as probes to identify related genes from other species such as, for example, various mammalian species which develop disorders involving aberrant ferritin and/or iron accumulation. As is well known in the art, hybridization stringencies may be adjusted to allow hybridization of nucleic acid probes with complementary sequences of varying degrees of homology. Thus, FTL variant polypeptide-encoding nucleic acids may be used to advantage to identify and characterize other genes of varying degrees of relation to FTL variant polypeptide, thereby facilitating the discovery of other variant ferritin proteins of utility in scientific research.

The FTL variant-encoding nucleic acids of the invention may also be used to identify genes encoding proteins that interact with FTL variant proteins (e.g., by the "interaction trap" technique), which should further accelerate identification of the components involved in FTL variant mediated neurodegeneration. The FTL variant-encoding nucleic acids may also be used to generate primer sets suitable for PCR amplification of target FTL variant DNA. Criteria for selecting suitable primers are well known to those of ordinary skill in the art.

Nucleic acid molecules, or fragments thereof, encoding a FTL variant gene may also be utilized to control the production of FTL variant polypeptide, thereby regulating the amount of protein available to participate in FTL variant-mediated iron accumulation and cellular degeneration. Antisense oligonucleotides corresponding to essential processing sites in FTL variant-encoding mRNA molecules may be utilized to inhibit FTL variant production in targeted host cells. Alterations in the physiological amount of FTL variant polypeptide may dramatically affect the ability of this protein to serve as a mediator of a neurological disorder.

As described above, FTL variant-encoding nucleic acids are also used to advantage to produce large quantities of substantially pure FTL variant protein, or selected portions thereof. The full-length protein or a selected domain can be used for research, diagnostic, and therapeutic purposes, as described below.

Host cells comprising a FTL variant encoding DNA molecules are encompassed in the present invention. Host cells contemplated for use in the present invention include but are not limited to bacterial cells, fungal cells, insect cells, mammalian cells, and plant cells. The FTL variant encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., *Current Protocols in Molecular Biology*, John Wiley & Sons, NY, N.Y. 1995, the disclosure of which is incorporated by reference herein.

A wide variety of expression vectors are available that can be modified to express the novel DNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/V5&His (Invitrogen); baculovirus vectors such as pVL1392, pVL1393, or pAC360 (Invitrogen); and yeast vectors such as YRP17, YIP5, and YEP24 (New England Biolabs, Beverly, Mass.), as well as pRS403 and pRS413 Stratagene Inc.); Picchia vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and *Saccharomyces* promoters such as the gal4 inducible promoter and the PGK constitutive promoter, as well as neuronal-specific platelet-derived growth factor promoter (PDGF), the Thy-1 promoter, the hamster and mouse Prion promoter (MoPrP), and the Glial fibrillar acidic protein (GFAP) for the expression of transgenes in glial cells.

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the FTL variant of the present invention or functional fragments thereof provide a system in which to screen potential compounds or agents for the ability to modulate FTL variant activity in a transformed cell. FTL variant modulating agents identified using such cellular systems may be used to advantage in the treatment of patients having a FTL variant gene-associated disorder. Such patients may be afflicted by the neurodegenerative disease described herein or other neurodegenerative diseases caused by alterations in proteins involved in iron metabolism. Other neurodegenerative diseases characterized by the presence of intranuclear aggregates include, for example, Huntington's disease, the spinocerebellar ataxias and other glutamine repeat disorders. Moreover, agents capable of modulating FTL variant activity, which are identified using the methods of the present invention, may also be used to advantage to treat diseases related to aberrant ferritin and/or iron deposition which affect other organ systems.

Thus, in one embodiment, the nucleic acid molecules of the invention may be used to create recombinant cell lines for use in assays to identify agents which modulate FTL variant mediated regulation of aberrant ferritin and iron deposition. Also provided herein are methods to screen for compounds capable of modulating FTL variant activity.

In another embodiment, the availability of FTL variant polypeptide-encoding nucleic acids enables the production of strains of laboratory mice carrying the FTL variant of the invention. Transgenic mice expressing the FTL variant of the invention provide a model system in which to examine the role of the FTL variant in the development and progression of a neurodegenerative disease. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that a target protein plays in various cellular processes, including: the intracellular accumulation of ferritin and/or iron, biochemical pathways involved in iron metabolism, and the development of degenerative disorders related to aberrant accumulation of intracellular iron, particularly those affecting the nervous system.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of FTL variant nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated FTL variant genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodouracil, (FIAU). By this counter selection, the number of homologous recombinants in the surviving transformants can be increased. Utilizing FTL variant as a targeted insertional cassette provides means to detect a successful insertion as visualized, for example, by acquisition of immunoreactivity to an antibody immunologically specific for FTL variant polypeptide and, therefore, facilitates screening/selection of ES cells with the desired genotype.

As used herein, a knock-in animal is one in which the endogenous murine gene, for example, has been replaced with human FTL variant gene of the invention. Such knock-in animals provide an ideal model system for studying the development of ferritinopathy.

As used herein, the expression of a FTL variant, fragment thereof, or a FTL variant fusion protein can be targeted in a "tissue specific manner" or "cell type specific manner" using a vector in which nucleic acid sequences encoding all or a portion of FTL variant are operably linked to regulatory sequences (e.g., promoters and/or enhancers) that direct expression of the encoded FTL variant protein in a particular tissue or cell type. Such regulatory elements may be used to advantage for both in vitro and in vivo applications. Promoters for directing tissue specific proteins are well known in the art and described herein. As discussed hereinbelow, expression of the FTL variant of the invention is related to aberrant liver cell function. Accordingly, the creation of transgenic animals which express the variant FTL gene specifically in the liver are useful for assessing agents which may modulate this form of the disorder.

The nucleic acid sequence encoding the FTL variant of the invention may be operably linked to a variety of different promoter sequences for expression in transgenic animals. Such promoters include, but are not limited to a prion gene promoter such as hamster and mouse Prion promoter (MoPrP), described in U.S. Pat. No. 5,877,399 and in Borchelt et al., Genet. Anal. 13(6) (1996) pages 159-163; a rat neuronal specific enolase promoter, described in U.S. Pat. Nos. 5,612,486, and 5,387,742; a platelet-derived growth factor B gene promoter, described in U.S. Pat. No. 5,811,633; a brain specific dystrophin promoter, described in U.S. Pat. No. 5,849,999; a Thy-1 promoter; a PGK promoter; a CMV promoter; a neuronal-specific platelet-derived growth factor B gene promoter; and Glial fibrillar acidic protein (GFAP) promoter for the expression of transgenes in glial cells. A particularly preferred promoter can be obtained from the MoPrP.xho vector described in Borchelt et al., above and obtainable from the ATCC JHU-2. Each of the forgoing patents and publications also provide detailed methods for the creation of transgenic animals in general, all of which are incorporated by reference herein.

Methods of use for the transgenic mice of the invention are also provided herein. Transgenic mice into which FTL variant or a FTL variant fusion protein have been introduced are useful, for example, to develop screening methods to screen therapeutic agents to identify those capable of modulating FTL variant activity.

The invention also provides a method of diagnosing a neurodegenerative disease in a patient or predicting a predisposition of a patient to a neurodegenerative disease. The method comprises detecting in a sample from a subject the presence of a mutation in a human ferritin light chain at a nucleotide position corresponding to codon 167 of a ferritin light chain or fragment thereof, wherein the presence of the mutation serves as a positive or diagnostic indicator of a neurodegenerative disease or a predisposition to a neurodegenerative disease. According to the present invention, detection of a nucleic acid sequence (e.g., SEQ ID NO: 1) which encodes an elongated FTL carboxy terminus also serves as a positive or diagnostic indicator of a neurodegenerative disease or a predisposition to a neurodegenerative disease.

There are many methods whereby a FTL light chain mutation of the present invention may be detected. Such methods are known to those of skill in the art and are described herein. For example, the detecting step can comprise combining a nucleotide probe capable of selectively hybridizing to a nucleic acid containing the mutation with a nucleic acid in a sample and detecting the presence of hybridization between the specific probe and a nucleic acid in the sample. The detecting steps may further comprise amplifying nucleic acids comprising the mutation and detecting the presence of the mutation in the amplified product. The detecting step may also comprise selectively amplifying the nucleic acids of the mutation and detecting the presence of amplification. Finally, the detecting step may comprise detecting the loss or creation of a restriction fragment length created using specific oligonucleotides followed by a restriction enzyme digest of the nucleic acid sequences of the mutation.

B. FTL Variant Polypeptides and Antibodies

As described above, nucleic acids encoding FTL variant protein may also be used to advantage to produce large quantities of substantially pure FTL variant protein, or selected portions thereof. FTL variant polypeptides may be used for a variety of purposes in accordance with the present invention.

After a DNA sequence encoding a FTL variant or a fragment thereof has been inserted into a vector, the vector may be used to transform a host cell. In general, the host cell may comprise any cellular organism including a prokaryotic cell or eukaryotic cell that is capable of being transformed with the vector comprising the DNA of the present invention. Techniques of transforming and transfecting cells are well known in the art and may be found in such general references as Sambrook et al. (1989) or Current Protocols in Molecular Biology (1989).

The present invention is not limited to use in a particular host cell. The vectors of the invention can be transformed into and expressed in many host cells. Transformed host cells of this invention may be cultured in conventional nutrient media modified as appropriate for inducing promoters, selecting transformants or amplifying genes. The culture conditions, such as temperature, pH and the like, are those previously used with the host cell selected for expression, and will be apparent to the ordinarily skilled artisan.

The choice of a particular host cell depends to some extent on the particular expression vector used to drive expression of a FTL variant. After transformation of a vector of the invention into a host cell one can select transformants on the basis of a selectable phenotype. This selectable phenotype can be conferred by a selectable marker present on the expression vector.

Suitable host cells include, for example, prokaryotic cells such as *Escherichia coli* and *Bacillus subtilis*; eukaryotic cells such as Mardin Darby canine kidney (MDCK) cells (American Type Culture Collection (ATCC CCL-34), Cos 7 cells (ATCC CRL-1651), 293 cells (ATCC CRL-1573), Chinese hamster ovary cells CHO-DHFR-(ATCC CRL-9096), Chinese hamster ovary cells CHO-K1 (ATCC CCL-61), Syrian Hamster cells AV12 (ATCC CRL 1573); yeast cells, including *Saccharomyces cerevisiae* and *Picchia pastoris*; insect cells including armyworm cells, such as *Spodoptera frugiperda* Sf9 (ATCC CRL 1711); and fungal cells including *Aspergillus* species.

Expression in prokaryotic and eukaryotic cells is described by Sambrook et al. (1989), and Kaufmann, Genetic Engineering Principles and Methods, ed. J. K. Setlow, Plenum Press 9:155, (1988). Yeast expression is described by Barr, et al., Yeast Genetic Engineering, eds. Butterworth, Boston 1989. Expression in insect cells is described by Maeda, 1989, Annual Review of Entomology 34:351.

As indicated above, the present invention provides methods for measuring FTL variant deposition, and FTL variant-mediated iron storage and detoxification in a cellular context. Such methods are applicable to the screening of compounds to test the ability of an individual compound or combination of compounds to modulate FTL variant activity in the above assays. Thus, one embodiment of this invention provides a method for assaying FTL variant activity in a cell having the following steps: a) contacting the compound with a cell that is transformed with a recombinant DNA expression vector which provides for expression of FTL variant activity, and b) assaying for modulation of FTL variant transcription, translation, and/or activity of the FTL variant in said cell.

Illustrative recombinant DNA expression vectors which provide expression of FTL variant activity that are useful in the method of this invention are described herein. Such recombinant DNA expression vectors can be tailored for optimal expression of FTL variant activity in a particular host cell.

A wide variety of cells, including those described above, may be used in this method. Cells that lack FTL variant activity before transformation with a recombinant DNA expression vector of this invention are especially useful in the method. Also useful are cells that possess measurable FTL variant activity before transformation with a recombinant DNA expression vector of this invention. In either case, cells that are transformed with a recombinant DNA expression vector encoding FTL variant activity can be assayed for FTL variant activity in the cell.

As noted above, the choice of vector used to express FTL variant will vary depending on the host cell that is utilized.

Purified FTL variant polypeptide, or fragments thereof, may be used to produce polyclonal or monoclonal antibodies which also may serve as sensitive detection reagents for the presence and accumulation of FTL variant proteins or complexes containing FTL variant proteins in mammalian cells. Recombinant techniques enable expression of fusion proteins containing part or all of the FTL variant polypeptide. The full length proteins or fragments thereof may be used to advantage to generate an array of monoclonal antibodies specific for various epitopes of these proteins, thereby providing additional assays for the detection of FTL variant protein or fusion proteins thereof in cells.

Polyclonal or monoclonal antibodies immunologically specific for FTL variant polypeptide may be used in a variety of assays designed to detect and quantitate FTL variant or fusion proteins thereof. Such assays include, but are not limited to: (1) flow cytometric analysis; (2) immunochemical localization of FTL variant proteins in cells; and (3) immunoblot analysis (e.g., dot blot, Western blot) of extracts from various cells. Additionally, as described above, anti-FTL variant polypeptide antibodies can be used for purification of said proteins or fusion proteins thereof (e.g., affinity column purification, immunoprecipitation).

Also provided are methods of use for the FTL variant specific antibodies described herein in diagnosing a neurodegenerative disease in a patient or predicting a predisposition of a patient to a neurodegenerative disease. The method comprises detecting in a sample from a subject the presence of a mutation in a human ferritin light chain polypeptide (e.g., a full length protein or fragment thereof) at amino acid position 167, wherein the presence of the mutation serves as a positive or diagnostic indicator of a neurodegenerative disease or a predisposition to a neurodegenerative disease. According to the present invention, detection of a amino acid sequence (e.g., SEQ ID NO: 2 or a fragment thereof) comprising an elongated FTL carboxy terminus also serves as a positive or diagnostic indicator of a neurodegenerative disease or a predisposition to a neurodegenerative disease.

From the foregoing discussion, it can be seen that FTL variant polypeptide-encoding nucleic acids, FTL variant polypeptide expressing vectors, FTL variant polypeptide and anti-FTL variant polypeptide antibodies of the invention can be used to detect FTL variant gene expression, alter FTL variant expression levels, modify FTL variant activity, and provide host cell and animal model systems that express FTL variant protein. Such systems provide assays for evaluating the role of FTL variant protein in an array of biological processes, including the onset and progression of a neurodegenerative disease, and for screening to identify agents capable of modulating FTL variant activity.

Although the compositions of the invention have been described with respect to human therapeutics, it will be apparent to one skilled in the art that these tools will also be useful in animal and cultured cell experimentation directed to investigating aberrant ferritin and iron deposition. As therapeutics, they can be used either alone or as adjuncts to other drugs for improving the effectiveness of such agents.

IV. Kits for Performing the Disclosed Methods

Kits are also provided to facilitate the detection of a FTL variant in biological samples. Exemplary approaches for detecting FTL variant nucleic acid or polypeptides/proteins include:

a) comparing sequences of nucleic acid in a sample with the FTL variant encoding nucleic acid sequence to determine whether the sample from the patient contains FTL variant sequences; or b) determining the presence, in a sample from a patient, of the polypeptide encoded by a FTL variant gene and, if present, determining whether the polypeptide is full length, and/or its expression level; or c) using DNA restriction mapping to compare the restriction pattern produced when a restriction enzyme cuts a sample of nucleic acid from the patient with the restriction pattern obtained from a normal FTL gene or from a FTL variant; or, d) using a specific binding member capable of binding to a FTL variant nucleic acid sequence, the specific binding member comprising nucleic acid hybridizable with the FTL variant sequence, or substances comprising an antibody domain with specificity for a FTL variant nucleic acid sequence or the polypeptide encoded by it, the specific binding member optionally being labeled so that binding of the specific binding member to its binding partner is detectable; or, e) using PCR involving one or more primers based on a FTL variant gene sequence to screen for a FTL variant gene in a sample from a patient.

In most embodiments for screening for a predisposition to a neurodegenerative disease, the FTL variant nucleic acid in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

The identification of the FTL variant gene and its association with neurodegenerative disease paves the way for aspects of the present invention related to the use of materials and methods, such as are disclosed and discussed above, for establishing the presence or absence in a test sample of a FTL variant gene. This may be useful for diagnosing a predisposition of an individual to a neurodegenerative disease or for diagnosing the type of neurodegenerative disease presented by a patient as being associated with the FTL variant gene.

In one broad aspect, the present invention encompasses kits for use in detecting expression of FTL variant in biopsy samples. Such a kit may comprise one or more pairs of primers for amplifying nucleic acids corresponding to the FTL variant gene. The kit may also comprise buffers, nucleotide bases, and other compositions to be used in hybridization and/or amplification reactions. Each solution or composition may be contained in a vial or bottle and all vials held in close confinement in a box for commercial sale.

Another embodiment of the present invention encompasses a kit for use in detecting FTL variant antigen in biopsy samples. Such a kit may comprise antibodies or antibody fragments immunologically specific for a FTL variant and means for assessing the formation of immunocomplexes containing the FTL variant.

V. Therapeutics

A. Rational Drug Design

Since the FTL variant of the present invention is associated with the development of aberrant intracellular deposition of FTL variant and ferritin heavy chain containing iron and is causally implicated in the development of a neurodegenerative disease, methods for identifying agents that modulate its activity are highly desirable. Such agents should have utility for the treatment of a variety of diseases, including neurodegenerative diseases characterized by the presence of intracellular aggregates and/or caused by alterations in proteins involved in iron metabolism. Moreover, agents capable of modulating FTL variant activity, which are identified using the methods of the present invention, may also be used to advantage to treat diseases related to aberrant ferritin and/or iron deposition which affect other organ systems.

The FTL variant polypeptide or fragment employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between a FTL variant polypeptide or fragment and the agent being tested, or examine the degree to which the formation of a complex between a FTL variant polypeptide or fragment and a known compound is interfered with by the agent being tested.

Another technique for drug screening provides high throughput screening for compounds having suitable binding affinity to FTL variant polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with FTL variant polypeptide and washed. Bound FTL variant polypeptide is then detected by methods well known in the art.

Another approach entails the use of phage display libraries engineered to express fragments of FTL variant on the phage surface. Such libraries are then contacted with a combinatorial chemical library under conditions wherein binding affinity between the FTL variant peptides and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides (e.g., a FTL variant polypeptide) may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based.

It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced peptides. Selected peptides would then act as the pharmacore.

Thus, it is clear from the foregoing that one may design drugs which act, e.g., as inhibitors, agonists, antagonists, etc. of FTL variant polypeptide activity. By virtue of the identification of a full length FTL variant clone as described herein, sufficient amounts of the FTL variant polypeptide may be made available to perform such analytical studies as x-ray crystallography. In addition, the knowledge of the FTL variant protein sequence provided herein will guide those employing computer modeling techniques in place of, or in addition to x-ray crystallography.

Suitable peptide targets for identifying specific FTL variant binding and modulating agents include, but are not limited to: the elongated carboxy terminus of the FTL variant of the invention comprising Ser-Ser-Lys-Gly-Ser-Leu-Ser-Ser-Thr-Thr-Lys-Ser-Leu-Leu-Ser-Pro-Ala-Thr-Ser-Glu-Gly-Pro-Leu-Ala-Lys (SEQ ID NO: 12).

B. Pharmaceuticals and Peptide Therapies

The identification of a full length FTL variant clone as described herein facilitates the development of pharmaceutical compositions useful for the development of optimal drugs for the treatment of patients with a variety of diseases, including neurodegenerative diseases. Utilizing methods of the present invention, such FTL variant activity-modulating drugs can be optimized for both the timing of delivery and maximal uptake in, for example, cells of the nervous system. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents, modulators, drugs (e.g., antibiotics) or hormones.

In preferred embodiments, the pharmaceutical compositions also contain a pharmaceutically acceptable excipient. Such materials should be non-toxic and should not interfere with the efficacy of the active ingredient. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., 18th Edition, Easton, Pa. [1990]). The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

The following examples are provided to illustrate certain embodiments of the invention. They are not intended to limit the invention in any way.

EXAMPLE I

As described hereinabove, ferritin is an iron storage protein made of 24 polypeptide chains which assemble into a hollow shell. In addition to its intracellular localization, ferritin is also secreted from cells and may act as an iron transport protein. In the brain, iron is normally involved in the biosynthesis of myelin. The distribution and composition of ferritin varies according to the region of the brain and the cell type therein. Brain ferritins are rich in heavy chains. Neuronal ferritin is mainly comprised of heavy chains, whereas light chain-rich ferritins are more commonly found in microglial cells. This variation in the FTH1:FTL ratio may have functional significance as a consequence of the specific activity of each subunit and the functional role of ferritin in these different cell types. Alternatively, the ratio may reflect differential regulation of the two ferritin chain genes in these cell types.

Ferritin is the principal protein for iron reserve, serving as a storage site for excess iron and for detoxification. Differences between the levels of ferritin and iron may be harmful for cells, since an increase in iron without a concomitant increase in ferritin may increase a cell's risk for oxidative stress. Accordingly, genetic studies have identified mutations in the ferritin genes as the key triggers for the pathogenesis of at least three different conditions, for example: I) mutations in the iron-responsive element (IRE) located in the 5'-noncoding region of the FTL chain gene have been associated with hereditary hyperferritinaemia (OMIN 600886), a disease characterized by dominantly inherited cataracts having an abnormally high level of serum ferritin; ii) a mutation in the IRE sequence of the FTH1 has been associated with the development of an autosomal dominant condition presenting with decreased levels of FTH1 and iron overload (OMIN 134770); and iii) a novel genetic defect in the coding region of the FTL gene was linked to the pathogenesis of an autosomal dominant basal ganglia disease designated "neuroferritinopathy". As described herein, individuals affected by neuroferritinopathy show extrapyramidal symptoms, low serum ferritin levels, and abnormal deposition of iron and ferritin in the basal ganglia (OMIN 606159).

A new hereditary neurodegenerative disease associated with a novel genetic defect in the coding region of the FTL gene is described herein. The disease was clinically characterized by tremor, cerebellar signs, extrapyramidal and pyramidal signs, behavioral disturbances and cognitive dysfunction. This symptomatology appears gradually over a period of four decades. Biochemical, genetic, and histological studies described herein revealed that this disorder is characterized by intranuclear and intracytoplasmic deposition of ferritin in glia and subsets of neurons in the central nervous system as well as in parenchymal cells of other organ systems. Further, these multidisciplinary studies revealed that the molecular genetic basis of the disorder is a novel mutation in the FTL gene leading to the production of a FTL with an abnormal carboxy terminus.

Material and Methods

Biopsy Studies. At separate times during the course of the disease, tissue biopsies (e.g., liver or skin) were derived from the proband. Tissue biopsies were also performed on cases III-11 (muscle and nerve), III-17 (kidney and skin) and IV-6 (skin). Tissue was processed for histological and electron microscopic studies according to established protocols. Eight μm-thick sections were stained with H&E and immunolabeled with anti-ferritin Abs (Dako and Biodesign) (1:500). Electron microscopic studies of the biopsy tissue were performed as described below.

Neurohistology. A post-mortem autopsy was performed on the proband (III-12). The fresh brain was hemisected along the sagittal plane; the right cerebral hemisphere, the right half of the cerebellum and the right half of the brain stem were fixed in 10% formalin. The left cerebral hemisphere, the left half of the cerebellum and the left half of the brain stem were sliced and stored at −70° C. for molecular genetic and biochemical analyses.

After fixation, tissue was obtained from superior frontal and cingulate gyri, superior parietal lobule, calcarine cortex, superior and middle temporal gyri, entorhinal cortex, hippocampus, amygdala, caudate nucleus, putamen, globus pallidus, thalamus, cerebellum, midbrain, pons and medulla of the right hemisphere. Following fixation, the tissue was dehydrated and embedded in paraffin. Eight μm-thick sections were stained using the following methods: hematoxylin and eosin (H&E), Congo red, thioflavin S, Woelcke-Heidenhan, Bodian, alcian blue, PAS and Pearls staining for iron.

Following a 72-h tissue fixation period, the left cerebral and cerebellar hemispheres and the left half of the brainstem were sliced. Tissue samples from the cerebral cortex, hippocampus, caudate nucleus, putamen, claustrum, globus pallidus, thalamus, amygdala, hypothalamus, subcortical nuclei, cerebellum, midbrain, pons, and medulla were dehydrated in graded alcohols, cleared in xylene, embedded in paraffin and 8-μm-thick sections were cut with a Leica rotary microtome. In addition, coronal slices were also processed for histology using a similar method and cut for whole mount on a Leica-Jung Polycut microtome. The sections were then stained with hematoxylin and eosin (H&E), the Heidenhain-Woelcke method for myelin, Bodian method for fibrils, thioflavin S for amyloid, alcian blue for mucopolysaccharides, periodic acid Schiff (PAS), and Pearls' method for ferric iron.

Production of antibodies. Polyclonal antibodies were generated by immunizing New Zealand White rabbits with either a synthetic peptide homologous to residues 166-175 (CLFERLTLKHD; SEQ ID NO: 4) of the FTL protein [antibody 1277] or a synthetic peptide (CLSSKGSLSST-TKSLLSPATSEGPLAK; SEQ ID NO: 5) [antibody 1283]

coupled to keyhole limpet hemocyanin via the N-terminal Cys of each peptide. After an initial subcutaneous (s.c.) injection of 200 μg of either antigen emulsified in Freund's complete adjuvant, animals were boosted with 50 μg of the appropriate antigen emulsified in Freund's incomplete adjuvant (Sigma) every 3 wk for 12 wk. The presence of specific antibodies was tested by ELISA.

Immunohistochemistry. Polyclonal antibodies (Abs) raised against human neuroserpin (1:2,000) (13), glial fibrillary acidic protein (GFAP) (Dako, Carpinteria, Calif.) (1:100), a synthetic peptide corresponding to residues 119-137 of human a-synuclein (1:300), ubiquitin (Dako) (1:1,000), ferritin (Dako and Biodesign, Saco, Me.) (1:500), ferritin heavy chain (Y-16) (Santa Cruz Biotechnology, Santa Cruz, Calif.) (1:50), polyglutamine (Chemicon, Temecula, Calif.) (1:500), and anti-ferritin Abs 1277 and 1283 (1:1,000), as were monoclonal Abs against the amyloid β protein (Aβ) (10D5) (Elan Corporation, San Francisco, Calif.) (1:100), calcium binding protein (a gift from Dr. M. Celio) (14) (1:500) and microtubule associated protein tau (AT8) (Pierce Biotechnology, Rockford, Ill.) (1:400). Tissue sections were incubated overnight at 4° C. with the primary Ab and then processed for staining. Double immunohistochemical studies were carried out using anti-ferritin Abs and anti-GFAP or anti-calcium binding protein to determine the localization and cell specificity of the ferritin accumulation. Polyclonal Abs were visualized by the peroxidase-antiperoxidase (PAP) method with goat anti-rabbit immunoglobulin (Ig) (or rabbit anti-goat Ig) and anti-rabbit PAP; monoclonal Abs were visualized using goat anti-mouse Ig and anti-mouse PAP; 3.3°-diaminobenzidine (DAB) was used as a chromogen.

Electron microscopy. Tissue obtained from frontal lobe (the superior frontal gyrus and the putamen) and cerebellum of the proband was fixed with 4% formaldehyde and post-fixed with 1% osmium tetroxide, dehydrated in grade alcohols, cleared in propylene oxide, and embedded in Epon. One-μm-thick sections were stained with toluidine blue. Ultrathin sections were contrasted with uranyl acetate and lead citrate and scanned with an electron microscope (EM, Philips EM 300).

Isolation, amino acid sequence and mass spectrometry of inclusions. Tissue was dissected from unfixed brain coronal sections of the cerebellum and putamen of the proband, cut with scissors into 1-3 mm pieces and placed in Dulbecco's-PBS (D-PBS, Sigma), with a cocktail of protease inhibitors (PIs) (Complete, 1 mM Pepstatin, 100 mM TLCK-HCl, 200 mM TPCK, and 1 mM Leupeptin, all from Roche, Indianapolis) on ice. As a control, cerebellar tissue from an unaffected individual was processed in the same manner. Tissue was washed by resuspension in D-PBS supplemented with PIs, and centrifuged at 5,000×g for 10 min at 4° C.; the procedure was repeated five times. The insoluble material was resuspended in 20 volumes of 2 mM $CaCl_2$ in 0.1 M Tris-HCl, pH 7.5, 3 mM $NaN_3$ and 2.0 mg/ml collagenase CLS-3 (Sigma) and 10 mg/ml DNase I (Sigma) were added, and the mixture was incubated for 18 h at 37° C. After digestion, the suspension was centrifuged at 5,000×g for 30 min at 4° C., washed three times with 0.1 M Tris-HCl (pH 7.4) and the insoluble-undigested material was subjected to three cycles of detergent washes in 1% n-lauryl sarcosine (Sigma). A final wash in the homogenization medium was performed and purified bodies were collected by centrifugation and viewed microscopically after H&E staining. This material was also fixed in 1% gluteraldehyde in phosphate buffer and post fixed in Dalton's chrome osmium, dehydrated in graded ethyl-alcohols, cleared in propylene oxide, and embedded in Poly/Bed®. Photographs were obtained using a Philips EM 300 electron microscope.

The purified bodies were solubilized in either 7% SDS, 300 mM Tris-HCl (pH 6.8), 36% glycerol (3× Solubilization Buffer or SB) or were incubated for 1 hour at room temperature with 99% formic acid (FA, Sigma), centrifuged at 10,000×g for 5 minutes and the supernatant dried under $N_2$. After solubilization, the supernatant fraction (SDS or FA) was separated on a 16% Tris-Tricine SDS PAGE, electrotransferred onto polyvinylidene difluoride membranes (PVDF; Immobilon-P, Millipore) using 10 mM 3-cycloexylamino-1-propanesulfonic acid (CAPS) buffer (pH 11), containing 10% methanol, and the corresponding band subjected to N-terminal sequence analysis on a 477A protein sequencer with an on-line 120A PTH analyzer (Applied Biosystems).

For mass spectrometry studies, the purified bodies were solubilized in water:isopropanol:formic acid (4:4:1) and subjected to matrix-assisted laser desorption/ionization time-of-flight (MALDI-TOF) mass spectrometry analysis (New York University Protein Analysis Facility at the Skirball Institute, New York University School of Medicine, New York).

Trypsin digestion, peptide fractionation and LCQ mass spectrometry. The SDS-supernatant fraction was separated by a 16% Tris-Tricine SDS PAGE. An ~22 KDa band was excised and digested in-gel with high performance liquid chromatography (HPLC)-grade trypsin. The tryptic peptides were purified on a Perkin Elmer Applied Biosystems capillary HPLC unit and subjected to LCQ quadruple ion trap mass spectrometry analysis using a Finnigan (Thermoquest) LCQ mass spectrometer (Biochemistry Biotechnology Facility, Indiana University School of Medicine). The peptide masses obtained were used to search the NCBI's nr protein sequence database using ProFound, in which a Bayesian algorithm is used to rank the protein sequences in the database according to their probability of producing the peptide map. Peptides corresponding to the obtained mass peaks were also identified by using the Protein Analysis WorkSheet (PAWS) freeware edition (proteometrics.com). Secondary structure prediction analysis was done at Jpred (Cuff and Barton, Proteins, 1999;40 502-11) and analysis for alpha helix context was done at ProtScale (Chou and Fasman, Adv Enzymol Relat Areas Mol Biol 1978;47:45-148).

Western Blot Analysis. Extracted inclusions were subjected to 16% acrylamide, tris-tricine-SDS PAGE. Recombinant human FTL and FTH1 (Calbiochem, San Diego, Calif.) were run as controls. Proteins were electrophoretically transferred for 1 hour (400 mA) at 4° C. to PVDF membranes (Immobilon-P, Millipore) using 10 mM CAPS buffer (pH 11), containing 10% methanol. The membranes were blocked with 5% non-fat dry milk in 10 mM phosphate buffer, 137 mM NaCl, 2.7 mM KCl (PBS) pH 7.4 with 0.1% Tween-20 (PBS-T) overnight and incubated for 2 hour at room temperature with primary antibody. The following primary antibodies were used: anti-ferritin antibody (Dako), anti-ferritin antibody (Biodesign), anti-FTH1(Y-16), antibody 1277, and antibody 1283. All antibodies were diluted (1:500) in PBS-T, unless otherwise indicated. Horseradish peroxidase-conjugated (HRP) goat anti-rabbit (Amersham) was used as a secondary antibody at a dilution of 1:5,000 in PBS-T. The Biodesign sheep-anti-ferritin antibody was preincubated with a polyclonal rabbit anti-sheep antibody (Chemicon) at a dilution of 1:500 in PBS-T. For the Y-16 antibody, anti-goat IgG-HRP (Santa Cruz Biotechnology) was used as the secondary antibody at a dilution 1:1,000. Immunoblots were visualized by chemiluminescence (Amersham) according to the manufacturer's specifications.

Molecular analyses. Genomic DNA was extracted from frozen brain tissue of the proband and from venous blood lymphocytes of 11 family members that included affected and non-affected individuals (II-3, II-5, III-11, III-22 to 27, IV-6, and IV-11). The entire coding sequence and exon-intron boundaries of the iron regulatory protein 1 (IRP1, or ACO1) and iron regulatory protein 2 (IRP2, or IREB2) were sequenced after establishing the organization and nucleotide sequence of both genes (R. Vidal, unpublished). The sequences of ACO1 human transcripts (GenBank Accession Nos. NM002197 and AF261088) were used in BLASTN homology searches (http://www.ncbi.nlm.nih.gov/BLAST/) to retrieve a human chromosome 9 clone containing the complete ACO1 gene sequence (RP11-334P12). The sequence of an IREB2 human transcript (GenBank Accession No. M58511) was used to retrieve a chromosome 15 genomic clone (GenBank Accession No. AC027228) containing the complete sequence of the IREB2 gene. The genomic sequence of FTL gene exons 1 and 2 (GenBank Accession No. X03742) and exons 3 and 4 (GenBank Accession No. X03743) and the sequence of FTH1 gene exon 1 (GenBank Accession No. M14211) and exons 2 to 4 (GenBank Accession No. M14212) was obtained by nucleotide searching at the National Center for Biotechnology Information (NCBI) (http://www.ncbi.nlm.nih.gov:80/entrez/).

Polymerase chain reaction (PCR) amplification was performed in 50-100 µl reactions containing 500 ng genomic DNA, 0.2 mM each DNTP, 1.5 mM $Mg_2Cl$, 0.5 µM each oligodeoxyclucleotide primer, 10 mM Tris-HCL, pH 8.3, 50 mM $KCl_2$ for 30 cycles of 94° C. 1 min, 45° C. 1 min and, 72° C. 2 minutes. The sequence of the oligonucleotide primers used in these experiments and the size of the obtained PCR products are provided in Table 1. PCR products were separated on either 1.5% agarose gels in TBE or 5% polyacrylamide gels in TBE and visualized by ethidium bromide staining. PCR fragments were gel purified (Qiagen Valencia, Calif.) and sequenced in both directions by direct DNA sequencing on a 377XL Applied Biosystem DNA sequencer (Biochemistry Biotechnology Facility, Indiana University School of Medicine) and with a CEQ 2000XL DNA analysis system (Beckman Coulter, Fullerton, Calif.). PCR products of FTL exon4 were subcloned into pCR2.1 vector (TA cloning kit, Invitrogen, Carlsbad, Calif.). Recombinant plasmid DNA was isolated from 8 to 10 clones generated in different PCR reactions and sequenced in both directions.

Table 1 lists primers of utility for PCR amplification of FTL genes

Reverse transcription-PCR (RT-PCR). Total cellular RNA was isolated from frozen brain tissue by the guanidine isothiocyanate method using Trizol LS (Invitrogen) reagent. Reverse transcription of RNA (1 µg) was performed with the Advantage RT-PCR kit (Clontech, Palo Alto, Calif.) using recombinant moloney murine leukemia virus (MMLV) reverse transcriptase with oligo(dT) or random hexamer primers. PCR amplification of the first strand cDNA produced by reverse transcription was performed using E1-2 forward oligonucleotide and E4 reverse oligonucleotide for the FTL gene. Each PCR cycle consisted of a denaturation step (94° C., 1 min), an annealing step (40° C., 2 min), and an elongation step (72° C., 3 min) and the cycle was repeated 30 times. RT-PCR products were separated on 1% agarose gels and visualized by ethidium bromide staining. RT-PCR products of FTL were subcloned into pCR2.1 vector (TA cloning kit, Invitrogen) and sequenced in both directions. As a positive control for the RT-PCR experiment, 0.45 kb of the housekeeping gene glyceraldehyde-3-phosphate-dehydrogenase (G3PDH; GAPD) was amplified using the Human G3PDH Control Amplimer Set (Clontech). As negative controls, RNA samples were pretreated with RNase A for 30 min at 37° C. and subjected to RT-PCR. In addition, RT-PCR experiments were performed for the FTH1 gene using oligonucleotides E1 forward and E4 reversed.

Results

Pedigree and Clinical evaluation of the proband. The family of the proband, identified here as "family L" has resided in Toulouse, France for several generations. A family pedigree was constructed based on available records which consisted of 56 members over 5 generations (FIG. 1). Individuals affected with the neurological disorder have been identified in four generations. The disease in this family appears to be inherited in an autosomal dominant pattern. The proband's (subject III-12) father (II-4), paternal aunt (II-7), brother (III-17), sister (III-11) and nephew (IV-6) were studied clinically and all presented neurological signs comparable to those of the proband. Subject III-11 underwent muscle and nerve biopsies; subject III-17 underwent kidney and skin biopsies; subject IV-6 underwent a skin biopsy. The biopsies showed the presence of intranuclear bodies in parenchymal cells of various tissues.

The proband (subject III-12) was a 59-year-old female. Neurological examinations of the proband were performed throughout the course of the disease. She first presented with tremor at age 20, mainly postural with functional impairment in writing. At age 41, the only symptom at full

| Gene | Exon | Primer sequence (5'-3') | | Product size (bp) |
|---|---|---|---|---|
| FTL | 1-2 | F: ACGTCCCCTCGCAGTTCGGCGG | (SEQ ID NO: 6) | 646 |
| | | R: TGTAGTCCATTACCCACAC | (SEQ ID NO: 7) | |
| | 3 | F: TGTAGGTTTAGTTCTATGTG | (SEQ ID NO: 8) | 275 |
| | | R: TGTGAATGAGGCTCTGAAGG | (SEQ ID NO: 9) | |
| | 4 | F: CTGTCACATTTTAATCTGCC | (SEQ ID NO: 10) | 293 |
| | | R: AAGCCCTATTACTTTGCAAG | (SEQ ID NO: 11) | |

F: forward primer; R: reverse primer. All primers are listed in 5'-3' orientation.

neurological examination was tremor, present when maintaining posture and during action, which was aggravated by emotion and stress. There was a mild tremor of the head, and the diagnosis was compatible with essential tremor, specifically in the context of a family history of tremor. A minor increase in liver transaminases and gamma GT was also observed, but was not clinically significant.

At age 47, the tremor presented similarly, but very slight signs of instability were also observed (such as, e.g., difficulties in walking along a straight line). EMG revealed a postural tremor, predominant in the left upper limb, but also present all four limbs, to a lesser degree in the lower limbs. Tremor frequency was 6 cycles/second, which was considered somewhat slow for a diagnosis of essential tremor. Due to the mild clinical ataxia, a CT scan was performed, which revealed moderate atrophy of the cerebellar vermis combined with mild sustentorial cortical atrophy. Liver enzymes remained unchanged.

By age 49, the tremor had worsened clinically, thereby rendering activities such as house keeping more difficult. Cerebellar signs became more prominent with typical dysarthria, dysmetria, and ataxia. No other signs were evident (e.g., no extrapyramidal, pyramidal or other syndrome was observed). CT scans revealed cerebellar atrophy, with no brainstem atrophy or ventricular dilatation.

By age 54, the tremor had progressed further. A resting tremor with a frequency of 4 cycles/min was also apparent, which predominantly affected the lower limbs, and was slower than a postural tremor. There was no evidence of hypertony or akinesia. Static and kinetic cerebellar syndrome was obvious, however, without indication of nystagmus and pyramidal involvement. The first signs of a subcortical-frontal cognitive impairment (disinhibition, difficulties in memory, mental calculation, verbal fluency, attention) were observed. A mini mental status exam (MMSE) was 26/30, memory quotient (MQ) 85/130 and dementia rating scale (DRS) 124/144. There was no autonomic system dysfunction, and normal blood pressure was recorded over a 24 hour period. CT scans showed progression of cerebellar atrophy, as well as cortical atrophy. MRI assessment revealed the same atrophy, but also detected abnormal T2 hypointense and T1 hyperintense signals in the basal ganglia, clinical features which resembled those of patients with MSA. The patient reported experiencing somnambulism. In view of the persistent liver changes, a study of copper metabolism was carried out and found to be normal. This finding combined with the history of a dominant inheritance ruled out Wilson disease as a possible diagnosis.

At age 55, a liver biopsy was performed to investigate the persistent liver enzymes abnormalities observed. The biopsy revealed signs of chronic active hepatitis with fibrosis, but without cirrhosis. In addition, intranuclear bodies were seen in fibroblasts within the portal spaces and intracytoplasmic deposits were present within hepatocytes located at the periphery of the lobules. The nature of the inclusions could not be established; however, a viral and toxic etiology of the liver dysfunction was ruled out.

By age 56, the patient exhibited further impairment in balance, but reported subjective improvement. Some very mild abnormal involuntary movement of the face, resembling tardive dyskinesia were noted. The first signs of parkinsonian hypertony with cogwheel rigidity were evident. Eye movements were normal.

By age 57, there was clear frontal cognitive syndrome, static and kinetic cerebellar syndrome, left predominant postural tremor, parkinsonian rigidity, and bucolingual dyskinesia. MRI showed cortical and subcortical, sus and subtentorial atrophy, involving the cerebellum and the pons. T2 hypointense and T1 hyperintense signals were seen in the caudate and lenticular nuclei. Oculography demonstrated normal horizontal and vertical saccades, but saccadic smooth pursuit (reduced gain), and abnormal VOR cancellation by fixation. There were no square wave jerks. Neuropsychology examination confirmed subcortical dementia.

At age 58, the patient considered that she was "stable", although she used a stick to help her walking. She had, however, fallen on several occasions and choreoathetosic dyskinesia of the limbs was apparent. She also presented with dystonic posture of the hands and feet when walking. Reflexes were brisk, and a left babinski sign was reported for the first time. The patient showed signs of depression.

By age 59, her clinical status deteriorated subacutely. Dyskinesia and dystonia of all four limbs disabled the patient and prevented normal feeding and walking. The patient, therefore, had to use a wheelchair. The patient also had insomnia. The patient was anxious and possessed normal insight with regard to her physical deterioration. Urinary incontinence, accompanied by urinary tract infection was observed. Haloperidol was administered to control the abnormal movements. Within a few weeks, however, a drug-related response led to the appearance of a major parkinsonian syndrome with global akinesia, hypertonia and severe resting tremor. Dysarthria and dysphagia were prominent. The patient could not perform any activity without assistance. Haloperidol administration was terminated. The parkinsonism improved, but the abnormal movements reappeared within few days. A trial with amantadine was subsequently planned, but the patient died of malnutrition and dehydration after two days in a coma.

Protein purification and characterization. Inclusions were isolated from frozen cerebellum and putamen of the proband by repeated cycles of homogenization-centrifugation in D-PBS followed by detergent washes. The quality and purity of the preparation was assessed by H&E staining (FIG. 2). After purification, the final insoluble fraction consisted of a high quantity of bodies that had a morphology comparable to that seen in tissue sections (FIG. 2A). Electron micrographs of the preparation revealed that bodies were composed of granular electron-dense particles measuring approximately 8.0 nm (FIG. 2B), which was of similar nature to that observed in the inclusions of the proband. Tris-tricine SDS-PAGE analysis of the purified SB solubilized inclusions revealed a major protein band migrating at a molecular weight (MW) of ~22 kDa in extracts from cerebellum (FIG. 2C, lane 3) and putamen (lane 4). In addition, a second band with a MW of ~44 kDa was observed. SDS-PAGE analysis of the material solubilized using FA revealed a predominant ~22 kDa protein band (not shown). Protein extracts prepared identically from the cerebellum of a control case did not show the presence of a ~22 KDa band (FIG. 2C, lane 2). Attempts to obtain direct N-terminal amino acid sequence of the ~22 kDa peptide failed, suggesting the presence of a blocked N-terminus. The ~22 KDa protein was subsequently digested with trypsin, the fragments were HPLC purified, and the mass of the tryptic peptides was determined by LCQ-mass spectrometry.

Peptide search of NCBI's nr protein sequence database using ProFound retrieved positive matches for light and heavy chains of ferritin (Table 2). Two tryptic peptides were of special interest. First, a tryptic peptide with a mass of 631.3 matched exactly the mass (631.7) of the amino terminal peptide of the FTL protein (SSQIR) having an acetyl group. This acetylated N-terminus precluded direct amino terminal sequencing by Edman degradation. Second, a peptide with a mass of 725.4 matched exactly the mass (725.4) of a C-terminal tryptic peptide corresponding to positions 170-175 (LTLKHD) of the FTL protein. Western blot studies using polyclonal antibodies raised against ferritin (Dako and Biodesign) specifically immunolabeled the two bands at ~22 and ~44 KDa (FIG. 2C, lane 5); the MW of these proteins corresponded to the MW of the proteins seen in Coomasie blue stain (FIG. 2C, lanes 3 and 4) and did not react with the preparation from a normal control. MALDI-TOF mass spectrometry analysis of the purified bodies showed the presence of two major peptides (FIG. 2D). A peptide with 19,933.7 units of mass (peak 1) matched exactly the estimated mass of a peptide encoded by the light chain of ferritin, with a post-translational modification at the N-terminus, which started at Ser 2 and had an N-terminal acetyl group. Such features were in accordance with the data obtained by LCQ mass spectrometry of the amino terminal tryptic peptide. The second major peptide (peak 2) had a molecular mass of 21,221.6, which matched the mass of full-length heavy chain ferritin as well as that of the mutant FTL. Table 2 shows measured/computed masses and identification of the tryptic peptides obtained after digestion of the purified inclusions.

| m/z measured/computed | Protein | Sequence |
| --- | --- | --- |
| 631.3/631.7 | FTL | 2-6 (+Ac) |
| 658.3/657.7 | FTH1 | 73-77 |
| 725.4/725.4 | FTL | 170-175 |
| 732.3/732.9 | FTL | 99-105 |
| 860.4/860.4 | FTL | 99-106 |
| 873.4/873.4 | FTL | 54-60 |
| 1,192.6/1,192.5 | FTL | 145-154 |
| 1,320.8/1,320.7 | FTL | 144-154 |
| 1,507.6/1,508.6 | FTL | 54-65 |
| 1,544.6/1,545.6 | FTH1 | 11-23 |
| 1,701.8/1,702.9 | FTL | 84-98/ 83-97 |
| 1,898.0/1896.0 | FTH1 | 65-80 |
| 1,938.6/1,935.2 | FTL | 61-76 |

Genetic analysis. The biochemical and neuropathologic data indicated that ferritin and iron were the main constituents of the inclusions, suggesting that a genetic defect in a protein involved in iron metabolism was implicated in the etiology of the disease. The coding regions and surrounding intronic sequences of the FTL and FTH1 genes and the two iron regulatory protein ACO1 and IREB2 genes in the proband were sequenced to evaluate their role as candidate causative genes for the novel neurodegenerative disease described herein.

ACO1 and IREB2 genes. The ACO1 gene is located on chromosome 9 (OMIM 100880) and is organized into 20 exons. IREB2 is located on chromosome 15 (OMIM 147582) and is organized into 22 exons. After PCR amplification, direct DNA sequencing of the entire coding sequence and adjacent intronic sequences of the ACO1 and IREB2 genes revealed wild-type sequences.

FTL and FTH1 genes. DNA sequencing of the iron response element (IRE) of the FTL and FTH1 genes, located in the 5'-untranslated region, revealed the presence of wild-type sequences. The nucleotide sequences of exons 1 to 4 of FTH1 and exons 1 to 3 of FTL were also normal (i.e., wild-type). PCR amplification and direct DNA sequencing of samples from affected members of family L revealed a cosegregating 2-bp insertion mutation detected after codon 166 (cDNA position 498), which was located in exon 4 of the FTL gene (FIGS. 3A and B). The mutation consists of a thymine (T) and a cytosine (C) insertion (TC sequence) between bases 498 and 499. PCR products containing the mutation were cloned and sequenced in both directions verifying the TC insertion (FIG. 3B). DNA sequence analysis showed the presence of the mutation in individuals III-11, III-12, III-24, III-25, III-27 and IV-6. The mutation was not found in individuals II-3, II-5, III-22, III-23, III-26 and IV-11, in 20 unrelated normal controls and after BLASTN searching of Expressed Sequence Tags (EST) databases.

Sequencing of cloned RT-PCR products revealed that the wild-type and mutant FTL genes (FIG. 3D) and the FTH1 gene were expressed in the brain of the proband. Nucleic acid sequences comprising the full length FTL variant gene (SEQ ID NO: 1), are provided herein (FIG. 4). Compared to the wild-type FTL protein of 175 amino acids, the mutant FTL protein has different amino acids at residues 167 to 175 and an additional 16 amino acids in positions 176 to 191 (FIG. 3C). Secondary structure prediction analysis and analysis for alpha helical context predict the loss the C-terminal secondary structure (α-helix) in the mutated FTL.

Western blot analysis of the purified protein bodies was carried out using an antibody specific for wild-type FTL (Ab 1277) and an antibody specific for mutant FTL (Ab 1283). The specificity of these antibodies was assessed using recombinant FTL and FTH1 (FIG. 3E, lanes 1-2,4-5). Neither antibody recognized recombinant FTH1 (lanes 1 and 4) and only Ab 1277 recognized recombinant FTL (lane 2). Both antibodies recognized the 22 kDa and 44 kDa proteins present in the isolated bodies (lanes 3 and 6).

The amino acid sequence of the full length FTL variant (SEQ ID NO: 2) is shown in FIG. 5. DNA sequencing of cloned FTL cDNAs obtained by RT-PCR (FIG. 3C) showed that both wild-type and mutant FTL alleles were expressed in the brain of the proband. Also provided herein is the nucleic acid sequence of the genomic FTL variant exon 4 (SEQ ID NO:3), shown in FIG. 6. Additionally, for the purposes of comparison, the nucleic acid sequence (SEQ ID NO: 13) and an amino acid sequence (SEQ ID NO: 14) of a wildtype FTL cDNA (FIG. 7A-B) are also provided.

Neuropathology.

Gross neuropathology. Further neuropathological studies were performed on the brain of the proband. The fresh brain of the proband weighed 1,120 g. There was no atherosclerosis in the major cerebral arteries; however, there was a whitish thickening of the endothelium. The cerebral hemispheres showed mild to moderate diffuse atrophy, which was most evident at the level of the frontal lobes where the sulci were dilated. In coronal sections, the lateral ventricles were mildly enlarged. The caudate nucleus and cerebellum were mildly atrophic and the brain stem appeared reduced in volume. The caudate nucleus and putamen had a grayish discoloration. The substantia nigra was hypopigmented. The spinal cord was not available for examination.

Neurohistology. Neuronal rarefaction was mild to moderate in the frontal, cingulate, temporal, parietal, insular, entorhinal and transentorhinal cortices, hippocampus, amygdala and thalamus. Gliosis was present throughout the cortical layers. Neuronal rarefaction and gliosis were most severe in the caudate nucleus, putamen and globus pallidus. In the putamen, loss of neurons led to the formation of cavities that have a longest dimension of up to 1.5 mm and appear to be confluent (FIG. 8). Moderate gliosis was present in the cerebral and cerebellar white matter. A mild to moderate loss of Purkinje cells was noted in the cerebellum. The substantia nigra and locus coeruleus showed mild neuronal rarefaction and gliosis. Amyloid deposits and neurofibrillary pathology were not detected in thioflavin S and Congo red preparations, or with immunostaining using antibodies specific for the Aβ (10D5) and Tau (AT8) proteins. With the Heidenhain-Woelcke staining method for myelin, pallor of the white matter of the frontal, temporal, parietal and occipital lobes was demonstrated.

The most striking pathologic alteration was the presence of intranuclear bodies in glial cells within most gray and white matter areas of the cerebrum, cerebellum and brain stem (FIG. 9-14, 17). In the cerebral cortex, intranuclear bodies were seen in perineuronal satellite cells. In the white matter, numerous glial cells were affected and their morphological characteristics had changed to such an extent that it was not possible to determine if they were astrocytes or oligodendroglial cells (FIG. 13). Intranuclear bodies in neurons were clearly recognizable only in the cerebellum, where the bodies were seen in the Purkinje cells and granule cells (FIG. 12). In Purkinje cells, bodies could be found in the cytoplasm as well; in fact, they were present in the perikaryon and dendrites (FIG. 12D, 12F-G). Often, both intranuclear and intracytoplasmic bodies could be seen within the same cell. In the caudate nucleus, putamen and globus pallidus, there were numerous bodies that appeared to be extracellular and larger than those bodies seen in glial cells (FIG. 11). These larger bodies seem to result from the coalescence of multiple bodies (FIG. 11C).

In most areas, the intranuclear bodies were eosinophilic and homogenous; however, in the caudate and putamen, the extracellular bodies appeared in clusters of eosinophilic or basophilic bodies. Throughout the brain, the bodies were stained using the Pearls' method for iron (FIG. 8B, 9B, 15E). The bodies were not stained by PAS. In Bodian preparations, the bodies were generally not argentophilic (FIG. 10B); however, in the caudate nucleus, putamen, globus pallidus and cerebellar cortex the bodies appeared as dark brown. The bodies were not stained with alcian blue and Heidenhain-Woelcke. They were not fluorescent in thioflavin S preparations. The bodies measured 2-35 μm in diameter. In many instances, the body occupied almost completely the nucleus and as a result displaced the chromatin up against the nuclear membrane (FIG. 10B-C, 12C-D). Many of the nuclei containing these bodies appeared larger than normal.

Intranuclear bodies were present in the nuclei of endothelial cells of arteries and veins (FIG. 15A, 15C). In addition, intranuclear bodies were seen in cells of the vascular adventitia (FIG. 15B). Often, in the perivascular space, mononuclear cells were seen containing intranuclear bodies (FIG. 15B). These bodies were also prominent in cells of the choroidal epithelium (FIG. 15D, 15E). Ependymal cells appeared to be free of intranuclear bodies.

Antibodies raised against ferritin strongly labeled intranuclear bodies of all sizes in glial cells and in nerve cells, specifically cerebellar Purkinje and granule cells (FIG. 9A, 10D-E, 11D-E, 12E-G, 13C, 13F). An important observation was that ferritin-immunopositivity was seen not only at the level of the intranuclear bodies but also in the cytoplasm of glial cells (9A, 10D-E, 12F-G, 13C, 13F). The cytoplasmic immunopositivity was diffuse in glia, but it was well-demarcated when present in Purkinje cells.

The ferritin-immunopositivity in nuclei and cytoplasms was present throughout the gray matter and white matter of the cerebral hemisphere, cerebellum and brain stem (FIG. 9A, 10D-E, 11D-E, 12E-G, 13C, 13F). Ferritin-immunopositive bodies were extremely abundant in the putamen (FIG. 11D-E). In the neocortex, the intranuclear and intracytoplasmic ferritin immunopositivity was present throughout the cortical layers, with the exception of layer I and II (FIG. 9A). Occasionally, ferritin immunopositivity was seen in the leptomeningeal and parenchymal vessel walls as well as in the leptomeningeal cells.

Using double immunohistochemistry for ferritin and GFAP, ferritin-immunopositive bodies of various sizes were seen in the nuclei of astrocytes; whereas, ferritin-immunopositive diffuse deposits were seen in astrocytic cytoplasms and processes that were also GFAP-immunopositive (FIG. 11E). In the cerebellum, double immunohistochemistry using Abs against calcium binding protein and ferritin demonstrated ferritin immunopositive bodies in cell processes and perikarya of Purkinje cells (FIG. 12G). In Purkinje cell dendrites, the ferritin immunopositive bodies were frequently seen at a considerable distance from the perikaryon. These bodies appeared more numerous in sections immunolabeled using ferritin antibodies than in those stained with hematoxylin and eosin. The intranuclear and intracytoplasmic bodies were also strongly immunopositive using an antibody raised against ubiquitin. The bodies did not immunoreact with antibodies against GFAP, polyglutamine, neuroserpin, tubulin, a-synuclein, amyloid β protein, and tau.

Electron microscopy. In toluidine blue-stained sections, the bodies appeared homogeneously dark or light blue (FIG. 10C, 11B-C, 12A-C, 13B, 13E, 15A-C). Low magnification electron micrographs revealed numerous electron-dense bodies within nuclei (FIG. 14A-E). In glial cells, bodies were occasionally seen in both nucleus and cytoplasm (FIG. 14E). In most cells, the bodies occupied a large portion of the nucleoplasm (FIG. 14A-E). In the neocortex, the material composing the bodies appeared to be less densely packed. Occasionally, a cluster of paracrystalline structures was seen within the intranuclear bodies. The chromatin appeared to be centrifugally displaced to varying degrees, often forming a thin layer adjacent to the nuclear membrane. The nuclei of the cerebellar granule cells contained deposits of various sizes and electron density (FIG. 14C-D). In high magnification electron micrographs, the bodies appear to be composed of granular electron-dense particles (FIG. 14B). The size of each particle was approximately 8.0 nm. The morphological features of the granular material were very similar to that previously reported for ferritin (Iancu T C. Electron Microsc Rev. 1992;5:209-29).

Dermatopathology, Renal Pathology & Muscle Pathology. Several biopsies obtained from multiple family members were reexamined using histology, immunohistochemistry and electron microscopy.

Dermatopathology. The epidermal cells did not appear to contain intranuclear bodies. On the contrary, numerous fibroblasts in the papillary dermis showed intranuclear bodies similar to those seen in cells of the central nervous system (FIG. 16A-B). The bodies were composed of fine granular material and occupied most of the nucleoplasm (FIG. 16B). Chromatin was confined to the periphery of the nucleus, forming a thin layer adjacent to the nuclear membrane. Using antibodies against ferritin, the intranuclear bodies were strongly labeled (FIG. 16C).

Renal Pathology. A small tissue sample containing only renal tubules, but not glomeruli showed the presence of ferritin-immunoreactive intranuclear bodies in the tubular epithelium (FIG. 16D).

Muscle Pathology. Intranuclear bodies appeared to be present in endothelial cells of muscle capillaries, but not nuclei of muscle cells.

Analysis of the Distribution of FTH1 and Wild-Type and Mutant FTL

Antibodies 1277 and 1283 were used to immunohistochemically study the distribution of wild-type and mutant FTL in the brain of the proband (FIG. 17). The pattern of immunohistochemical labeling of the intranuclear and intracytoplasmic ferritin deposits was practically indistinguishable from the pattern seen in sections immunolabeled using the anti-ferritin Abs obtained from Dako and Biodesign (FIG. 17A-D). In addition, immunohistochemical studies using Ab Y-16, raised against FTH1, showed that FTH1 was also present in the deposits (FIG. 17E-F).

DISCUSSION

Eleven individuals across four generations of a French family had a disease characterized by tremor, ataxia, extrapyramidal and pyramidal signs, behavioral disturbances, and cognitive decline. Pathology studies on the proband revealed intranuclear and intracytoplasmic bodies in glia and some subsets of neurons throughout the central nervous system as well as in cells of other organ systems. Histochemically, these bodies were shown to have a high content of iron. Biochemical and immunohistochemical analyses showed that the main constituent of bodies was ferritin. Molecular genetic analysis revealed an insertion mutation in exon 4 of the FTL gene of the proband and five other affected individuals from whom DNA was available. We have called this disorder hereditary ferritinopathy.

The neuropathologic data show that ferritin accumulation is associated with a mild to moderate degree of cerebral and cerebellar atrophy and with severe degenerative changes of the caudate nucleus and putamen, leading to tissue cavitation. The wide distribution of ferritin bodies in the central nervous system reflects the ubiquitous expression of this protein in the human brain; however, the severity of ferritin accumulation varies. Gray and white matter regions are equally affected; however, the striatum carries the brunt of the disease. The cortical and subcortical pathology correlates well with the progressive deterioration in cognitive function and severe extrapyramidal symptomatology. The cerebellar pathology correlates with the progressive ataxia. In the proband, it was found that ferritin bodies are present in the nucleus of glial cells, choroidal epithelial cells and subsets of neurons. Immunohistochemistry and electron microscopy revealed the presence of ferritin in the cytoplasm; however, the cytoplasmic ferritin is not forming bodies that are as well demarcated as those bodies in the nuclei. Of the glial cells, affected oligodendrocytes are seen throughout whereas affected astrocytes are seen mostly in the striatum and cerebellum. In the latter, the Golgi epithelial cells were the most severely affected. Choroidal epithelial cells are known to contain transferrin, iron and ferritin (Connor J R, et al. Pediatr Neurol. 2001;25:118-29); therefore, in view of the presence of ferritin bodies in these cells, it is likely that a dysfunction in the production of CSF may occur in this disorder. Among neurons, Purkinje cells and cerebellar granule cells have ferritin bodies in the nucleus. Purkinje cells have prominent bodies also in the cytoplasm of the perikaryon and dendrites. The presence of ferritin bodies only in certain neuronal populations suggests that nerve cells may have differences in ferritin expression and/or in their ability of clearing from abnormal ferritin.

Extracellular deposits were only seen in the caudate nucleus, putamen and globus pallidus, which are known to normally contain the largest amount of ferritin and iron in the brain (Benkovic S A, et al. J Comp Neurol. 1993;338: 97-113). These extracellular deposits appear to be the result of the confluence of intracellular bodies, either intranuclear or intracytoplasmic or both, following the rupture of the nuclear and cell membranes. The ferritin-induced cellular damage in the striatum is very severe and leads to cell loss. The intraparenchymal cavities seen in the striatum may be a result of cell degeneration, formation of extracellular bodies and loss of neuropil. It can be hypothesized that tissue cavitation results from the lack of ability of the affected astrocytes to react to injury.

The biochemical and neuropathologic data indicated that the main constituent of the bodies was ferritin, suggesting that the cause of the disease was a genetic defect in a protein associated with iron metabolism. The coding regions and surrounding intronic sequences of ACO1, IREB2, FTH1, and FTL genes were sequenced. The ACO1 and IREB2 genes were analyzed because a neurodegenerative disorder clinically and pathologically similar to hereditary ferritinopathy had been reported in a mouse generated with a targeted deletion of the gene encoding iron regulatory protein 2 (Ireb2). The mouse develops a movement disorder characterized by ataxia, bradykinesia and tremor (LaVaute T. et al. Nat Genet 2001;27:209-14.). Adult Ireb2-deficient mice show a significant accumulation of iron in the white and gray matter and an overexpression of ferritin in Purkinje cells. In the absence of a mutation in those two genes, further studies led to the discovery of a TC-insertion mutation in the FTL gene.

Biochemical and immunohistochemical studies revealed that bodies contained wild-type and mutant FTL as well as FTH1. In the physiological state, ferritin is composed of FTL and FTH1 (Harrison P M, et al. Biochim Biophys Acta 1996; 1275:161-203). At the three-dimensional level, each ferritin polypeptide (FTL and FTH1) consists of a bundle of four long helices, a fifth short helix and a long extended loop (Harrison P M, et al. Biochim Biophys Acta 1996; 1275: 161-203; Hempstead P D, et al. J Mol Biol 1997;268:424-48.). The α-helical domains, named A, B, C, D, and E, correspond approximately to residues 12 to 39, 47 to 73, 94 to 121, 126 to 155 and 162 to 175 of the amino acid sequence of FTL, respectively. The wild-type FTL polypeptide consists of 175 amino acids; whereas, the mutant FTL polypeptide, present in the individuals affected by hereditary ferritinopathy, consists of 191 amino acids. The mutant FTL has different amino acids at residues 167 to 175 and an additional 16 amino acids at residues 176 to 191 as compared to the wild-type.

Ferritin can be seen by electron microscopy as tiny dense particles dispersed in the cytosol of the cells (Iancu T C. et al., Electron Microsc Rev. 1992;5:209-29). Data regarding the presence of ferritin in the cell nucleus are limited. Ferritin has been shown to be present in the nucleus of human astrocytoma cells (Thompson K J, et al. J Cell Sci 2002;115:2165-77), avian corneal epithelial cells (Cai C X, et al. J Biol Chem 1997;272:12831-9; Cai C X, et al. J Cell Sci. 2001;114:2327-34) and cells in animal models of iron overload (Ladda R. Exp Cell Res. 1962; 28:595-597; Moore R D, et al. J Ultrastruct Res 1961;5:244-256; Kondo A, et al. Virchows Arch 1998;433:543-8; Haddow A, et al. J Natl Cancer Inst. 1960; 24:109-147; Goetz W, et al. J. Biophysic Biochem Cytol. 1961;9:263-270; Smith A G, et al., Hepatology 1990;12:1399-405; Iancu T C, et al. J Hepatol 1985; 1:261-75). Since ferritin does not have any known nuclear localization signals (NLS) and is not affected by inhibitors of the translocation of NLS-containing proteins (Thompson K J, et al. J Cell Sci 2002;115:2165-77), the mechanism of transport of ferritin to the nucleus and its specific role in the cell nucleus in these pathologic conditions remains unknown (Thompson K J, et al. J Cell Sci 2002;115:2165-77, Pountney D, et al., J Cell Sci. 1999;112:825-31). Using FTH1-myc-tagged constructs having C-terminal deletions and therefore no E helix, (Cai C X, et al. J Cell Sci. 2001;114: 2327-34) showed nuclear transport without supramolecular assembly of ferritin into the nucleus of corneal epithelial cells. This suggests that supramolecular assembly is not necessary for nuclear transport to occur and that transport does not need the presence of the E-helix domain.

Recently, an autosomal dominant disease resulting from an adenine insertion at position 460-461 in the FTL gene has been described in English and French families (Curtis A R, et al., Nat Genet. 2001;28:350-4; Crompton D E, et al. Blood Cells Mol Dis. 2002;29:522-31; Chinnery P F, et al. J Med Genet. 2003;40:e69). The disorder, named neuroferritinopathy, is characterized by dystonia and low serum ferritin levels as well as basal ganglia cavitation and deposition of ferritin and iron. Although some of these characteristics are seen in individuals affected by hereditary ferritinopathy, several significant observations differentiate the disorders. First, the age of onset in hereditary ferritinopathy is in the third decade while that seen in neuroferritinopathy is generally in the fifth and sixth decade. Second, the cellular localization of ferritin deposition differs between the two disorders. In fact, an intranuclear localization has not been described in neuroferritinopathy; whereas, it is a predominant characteristic in hereditary ferritinopathy. Third, the cerebellar pathology in hereditary ferritinopathy seems to be much more severe that than described in neuroferritinopathy. Fourth, several extra neural systems are involved in hereditary ferritinopathy. It is not clear whether this is the case in neuroferritinopathy since data on systemic pathology has not been reported.

Both hereditary ferritinopathy and neuroferritinopathy are associated with mutations that alter the C-terminal-amino-acid sequence of FTL. These alterations presumably result in the accumulation of ferritin. The mutations may cause a change in the secondary structure of the protein. In hereditary ferritinopathy, the mutant FTL polypeptide appears to have lost the last α-helical domain (E); in neuroferritinopathy, the mutant FTL polypeptide is predicted to lack the end of the D helix, the D-E loop and the E helix (Curtis A R, et al., Nat Genet. 2001;28:350-4; Crompton D E, et al. Blood Cells Mol Dis. 2002;29:522-31). These conformational changes may have a significant impact in the structure of the FTL and the stability of the ferritin molecules. The E helix appears to stabilize the subunit conformation of ferritin making several hydrophobic contacts with apolar side chains near the start of helix B and the end of D as well as being linked by hydrogen bonds to the N-terminal ends of helices B and C (Harrison P M, et al., Biochim Biophys Acta 1996; 1275:161-203.; Granier T, et al. Acta Crystallogr D Biol Crystallogr 2001;57:1491-7; Jappelli R, et al. J Mol Biol 1992;227:532-43). Point mutations in the E helix of FTH1 lead to the aggregation of ferritin by either preventing the full assembly of the protein or by causing the precipitation of entirely assembled molecules (Jappelli R, et al. J Mol Biol 1992;227:532-43; Jappelli R, et al. Biochem Biophys Res Commun 1998;250:342-6). The latter appears to occur in hereditary ferritinopathy based on the following observations: 1) identification of ferritin as the major constituent of the bodies, 2) presence of FTH1, wild-type FTL and mutant FTL in the bodies and 3) particles resembling ferritin are the main constituents of the bodies as seen by electron microscopy.

The altered C terminal of FTL may also alter the ability of ferritin to carry out, normally, its function as an iron storage protein. It has been hypothesized for neuroferritinopathy that ferritin may not be able to store iron properly leading to an excess of intracellular iron (Crompton D E, et al. Blood Cells Mol Dis. 2002;29:522-31). This excess iron may cause an increase in the translation of the ferritin polypeptides leading to ferritin and iron overload. This mechanism may also be responsible for the ferritin and iron overload seen in hereditary ferritinopathy.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A transgenic mouse whose genome comprises an altered ferritin light chain encoded by SEQ ID No. 1, wherein nucleotide sequence of SEQ ID No. 1 is operably linked to the mouse MoPrP prion promoter, and wherein said mouse exhibits aberrant accumulation of ferritin and iron in the cells of the central nervous system.

2. A method for screening and identifying agents which affect aberrant accumulation of ferritin and iron in cells of the central nervous system in the transgenic mouse of claim 1, comprising:

a) administering said agent to said transgenic mouse;
b) assessing said mouse for an alteration in aberrant ferritin and iron accumulation, if any, relative to an untreated mouse, and
c) identifying those agents which modulate accumulation of said ferritin and iron.

3. The method of claim 2, wherein said mouse is assessed for aberrant iron and ferritin accumulation via histochemistry of brain.

4. A host cell isolated from the transgenic mouse of claim 1.

* * * * *

UNITED STATES PATENT AND TRADEMARK OFFICE
CERTIFICATE OF CORRECTION

| | | |
|---|---|---|
| PATENT NO. | : 7,332,643 B2 | Page 1 of 1 |
| APPLICATION NO. | : 10/684742 | |
| DATED | : February 19, 2008 | |
| INVENTOR(S) | : Bernardino Ghetti and Ruben Vidal | |

It is certified that error appears in the above-identified patent and that said Letters Patent is hereby corrected as shown below:

Column 1, Lines 11-14 appear
"Pursuant to 35 U.S.C. §202(c), it is acknowledged that the U.S. Government has certain rights in the invention described, which was made in part with funds from PHS grants P30AG10133 and U01AG16976"

should be

--Pursuant to 35 U.S.C. §202(c), it is acknowledged that part of the work during the development of this invention was made with government support from the National Institutes of Health under grants AG010133, AG016976 and NS014426. The U.S. government has certain rights in the invention described.--

Signed and Sealed this

Third Day of June, 2008

JON W. DUDAS
*Director of the United States Patent and Trademark Office*

SEQUENCE LISTING

```
<160> NUMBER OF SEQ ID NOS: 14

<210> SEQ ID NO 1
<211> LENGTH: 576
<212> TYPE: DNA
<213> ORGANISM: Homo sapien

<400> SEQUENCE: 1
atgagctccc agattcgtca gaattattcc accgacgtgg aggcagccgt caacagcctg      60
gtcaatttgt acctgcaggc ctcctacacc tacctctctc tgggcttcta tttcgaccgc     120
gatgatgtgg ctctggaagg cgtgagccac ttcttccgcg aattggccga ggagaagcgc     180
gagggctacg agcgtctcct gaagatgcaa aaccagcgtg gcggccgcgc tctcttccag     240
gacatcaaga agccagctga agatgagtgg ggtaaaaccc cagacgccat gaaagctgcc     300
```

```
atggccctgg agaaaaagct gaaccaggcc cttttggatc ttcatgccct gggttctgcc    360
cgcacggacc cccatctctg tgacttcctg gagactcact tcctagatga ggaagtgaag    420
cttatcaaga gatgggtga ccacctgacc aacctccaca ggctgggtgg cccggaggct    480
gggctgggcg agtatctctc ttcgaaaggc tcactctcaa gcacgactaa gagccttctg    540
agcccagcga cttctgaagg ccccttgca aagtaa                                576
```

```
<210> SEQ ID NO 2
<211> LENGTH: 191
<212> TYPE: PRT
<213> ORGANISM: Homo sapien

<400> SEQUENCE: 2
```

Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
                20                  25                  30

Ser Leu Gly Phe Tyr Phe Asp Arg Asp Asp Val Ala Leu Glu Gly Val
            35                  40                  45

Ser His Phe Phe Arg Glu Leu Ala Glu Glu Lys Arg Glu Gly Tyr Glu
        50                  55                  60

Arg Leu Leu Lys Met Gln Asn Gln Arg Gly Gly Arg Ala Leu Phe Gln
65                  70                  75                  80

Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu His Arg Leu Gly Gly Pro Glu Ala
145                 150                 155                 160

Gly Leu Gly Glu Tyr Leu Ser Ser Lys Gly Ser Leu Ser Ser Thr Thr
                165                 170                 175

Lys Ser Leu Leu Ser Pro Ala Thr Ser Glu Gly Pro Leu Ala Lys
            180                 185                 190

```
<210> SEQ ID NO 3
<211> LENGTH: 60
<212> TYPE: DNA
<213> ORGANISM: Homo sapien

<400> SEQUENCE: 3
ctctgtgact tcctggagac tcacttccta gatgaggaag tgaagcttat caagaagatg    60

<210> SEQ ID NO 4
<211> LENGTH: 11
<212> TYPE: PRT
<213> ORGANISM: Homo sapien

<400> SEQUENCE: 4
```

Cys Leu Phe Glu Arg Leu Thr Leu Lys His Asp
1               5                   10

```
<210> SEQ ID NO 5
<211> LENGTH: 27
<212> TYPE: PRT
<213> ORGANISM: Homo sapien

<400> SEQUENCE: 5

Cys Leu Ser Ser Lys Gly Ser Leu Ser Ser Thr Thr Lys Ser Leu Leu
 1               5                  10                  15

Ser Pro Ala Thr Ser Glu Gly Pro Leu Ala Lys
            20                  25

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
acgtcccctc gcagttcggc gg                                                22

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
tgtagtccat tacccacac                                                    19

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
tgtaggttta gttctatgtg                                                   20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tgtgaatgag gctctgaagg                                                   20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ctgtcacatt ttaatctgcc                                                   20

<210> SEQ ID NO 11
<211> LENGTH: 20
<212> TYPE: DNA
<213> ORGANISM: Artificial Sequence
```

-continued

```
<220> FEATURE:
<223> OTHER INFORMATION: primer

<400> SEQUENCE: 11
aagccctatt actttgcaag                                                  20

<210> SEQ ID NO 12
<211> LENGTH: 25
<212> TYPE: PRT
<213> ORGANISM: Homo sapien

<400> SEQUENCE: 12

Ser Ser Lys Gly Ser Leu Ser Ser Thr Thr Lys Ser Leu Leu Ser Pro
 1               5                  10                  15

Ala Thr Ser Glu Gly Pro Leu Ala Lys
             20                  25

<210> SEQ ID NO 13
<211> LENGTH: 600
<212> TYPE: DNA
<213> ORGANISM: Homo sapien

<400> SEQUENCE: 13
ccaaccatga gctcccagat tcgtcagaat tattccaccg acgtggaggc agccgtcaac      60
agcctggtca atttgtacct gcaggcctcc tacacctacc tctctctggg cttctatttc     120
gaccgcgatg atgtggctct ggaaggcgtg agccacttct ccgcgaattg gccgaggag      180 aagcgcgagg gctacgagcg tctcctgaag atgcaaaacc agcgtggcgg ccgcgctctc     240
ttccaggaca tcaagaagcc agctgaagat gagtggggta aaccccagac gccatgaaa     300 gctgccatgg ccctggagaa aaagctgaac caggcccttt tggatcttca tgccctgggt     360
tctgcccgca cggacccca tctctgtgac ttcctggaga ctcacttcct agatgaggaa      420
gtgaagctta tcaagaagat gggtgaccac ctgaccaacc tccacaggct gggtggcccg     480
gaggctgggc tgggcgagta tctcttcgaa aggctcactc tcaagcacga ctaagagcct     540
tctgagccca gcgacttctg aagggccct tgcaaagtaa tagggcttct gcctaagcct      600

<210> SEQ ID NO 14
<211> LENGTH: 175
<212> TYPE: PRT
<213> ORGANISM: Homo sapien

<400> SEQUENCE: 14

Met Ser Ser Gln Ile Arg Gln Asn Tyr Ser Thr Asp Val Glu Ala Ala
 1               5                  10                  15

Val Asn Ser Leu Val Asn Leu Tyr Leu Gln Ala Ser Tyr Thr Tyr Leu
             20                  25                  30

Ser Leu Gly Phe Tyr Phe Asp Arg Asp Asp Val Ala Leu Glu Gly Val
         35                  40                  45

Ser His Phe Phe Arg Glu Leu Ala Glu Glu Lys Arg Glu Gly Tyr Glu
     50                  55                  60

Arg Leu Leu Lys Met Gln Asn Gln Arg Gly Gly Arg Ala Leu Phe Gln
 65                  70                  75                  80

Asp Ile Lys Lys Pro Ala Glu Asp Glu Trp Gly Lys Thr Pro Asp Ala
                 85                  90                  95

Met Lys Ala Ala Met Ala Leu Glu Lys Lys Leu Asn Gln Ala Leu Leu
            100                 105                 110
```

-continued

| | | | | | | | | | | | | | | |
|---|---|---|---|---|---|---|---|---|---|---|---|---|---|---|
| Asp | Leu | His | Ala | Leu | Gly | Ser | Ala | Arg | Thr | Asp | Pro | His | Leu | Cys | Asp |
| | | 115 | | | | | 120 | | | | 125 | | | | |
| Phe | Leu | Glu | Thr | His | Phe | Leu | Asp | Glu | Glu | Val | Lys | Leu | Ile | Lys | Lys |
| | | 130 | | | | 135 | | | | 140 | | | | | |
| Met | Gly | Asp | His | Leu | Thr | Asn | Leu | His | Arg | Leu | Gly | Gly | Pro | Glu | Ala |
| 145 | | | | | 150 | | | | | 155 | | | | | 160 |
| Gly | Leu | Gly | Glu | Tyr | Leu | Phe | Glu | Arg | Leu | Thr | Leu | Lys | His | Asp | |
| | | | | 165 | | | | | 170 | | | | | 175 | |